(12) United States Patent
Cronyn

(10) Patent No.: US 8,124,793 B2
(45) Date of Patent: Feb. 28, 2012

(54) DERIVATIVES OF ETHYLENE METHANEDISULFONATE AS CANCER CHEMOTHERAPEUTIC AGENTS

(76) Inventor: Marshall W. Cronyn, Portland, OR (US); Gail Marie Cronyn, legal representative, Portland, CA (US); Lori Ruth Cronyn, legal representative, Beverly Hills, CA (US)

(*) Notice: Subject to any disclaimer, the term of this patent is extended or adjusted under 35 U.S.C. 154(b) by 526 days.

(21) Appl. No.: 12/324,785

(22) Filed: Nov. 26, 2008

(65) Prior Publication Data

US 2009/0176805 A1    Jul. 9, 2009

Related U.S. Application Data

(60) Provisional application No. 60/990,561, filed on Nov. 27, 2007.

(51) Int. Cl.
*C07D 339/00*    (2006.01)
(52) U.S. Cl. .......................................... 549/11
(58) Field of Classification Search ............. 549/11
See application file for complete search history.

(56) References Cited

U.S. PATENT DOCUMENTS

| | | |
|---|---|---|
| 3,275,672 A | 9/1966 | Kühne et al. |
| 3,960,870 A | 6/1976 | Blackburn et al. |
| 4,199,513 A | 4/1980 | De Jong et al. |
| 4,340,531 A | 7/1982 | Wegmann |
| 4,344,945 A | 8/1982 | Teranishi et al. |
| 4,344,948 A | 8/1982 | Takai et al. |
| 4,390,536 A | 6/1983 | Teranishi et al. |
| 4,410,528 A | 10/1983 | Teranishi et al. |
| 4,483,799 A | 11/1984 | Kampfer et al. |
| 4,575,497 A | 3/1986 | Omura et al. |
| 4,668,683 A | 5/1987 | Takai et al. |
| 4,719,055 A | 1/1988 | Bair |
| 4,879,386 A | 11/1989 | Saito et al. |
| 4,946,957 A | 8/1990 | Saito et al. |
| 4,950,768 A | 8/1990 | Cronyn |
| 4,992,551 A | 2/1991 | Saito et al. |
| 5,071,984 A | 12/1991 | Saito et al. |
| 5,175,301 A | 12/1992 | Minamida et al. |
| 5,214,152 A | 5/1993 | Minamida et al. |
| 5,364,989 A | 11/1994 | Aoki et al. |
| 5,849,768 A | 12/1998 | Minamida et al. |
| 5,877,325 A | 3/1999 | Löffler et al. |
| 5,935,981 A | 8/1999 | Minamida et al. |
| 5,952,283 A | 9/1999 | Löffler et al. |
| 6,028,047 A | 2/2000 | Nestler |
| 6,030,840 A | 2/2000 | Mullinax et al. |
| 6,124,297 A | 9/2000 | Minamida et al. |
| 6,384,049 B1 | 5/2002 | Camden |
| 6,407,248 B1 | 6/2002 | Minamida et al. |
| 6,498,133 B2 | 12/2002 | Borchers et al. |
| 6,949,501 B2 | 9/2005 | Himmrich et al. |
| 7,005,534 B2 | 2/2006 | Schreiber et al. |
| 7,015,185 B2 | 3/2006 | Seebach et al. |
| 7,268,130 B2 | 9/2007 | Desos et al. |
| 7,332,464 B2 | 2/2008 | Cramer et al. |
| 7,342,027 B2 | 3/2008 | Lee et al. |
| 2009/0176805 A1 | 7/2009 | Cronyn |

FOREIGN PATENT DOCUMENTS

| | | |
|---|---|---|
| AT | 210874 B | 8/1960 |
| DE | 1124032 B | 2/1962 |
| GB | 700677 A | 12/1952 |

OTHER PUBLICATIONS

Gibson, Characterization of DNA Damage and Cytotoxicity Induced in Two Human Colon Carcinoma Cell Lines by Cyclodisone, 1989, Cancer Research, vol. 49(1), p. 154-157.*
Golub et al., Molecular Classification of Cancer: Class Discovery and Class Prediction by Gene Expression Monitoring. Science, vol. 286, Oct. 15, 1999, p. 531-537.*
Target Cancer Therapies, http://www.cancer.gov/cancertopics/factsheet/therapy/targeted, accessed Jan. 12, 2011.*
Voskoglou-Nomikos et al, Clincial Predictive Value of the in Vitro Cell line, Human Xenograft, and Mouse Allograft Preclinical Cancer Models, Sep. 15, 2003, Clnical Cancer Research, vol. 9, p. 4227-4239.*
Hung, Su H. et al., "A new nonhydrolyzable reactive cGMP analogue, (Rp)-guanosine-3', 5'-cyclic-S-(4-bromo-2,3-dioxobutyl)monophosphorothioate, which targets the cGMP binding site of human platelet PDE3A," Bioorganic Chemistry 36 (2008) 141-147, 7 pages.
Weinstein, John N. et al., "Neural Computing in Cancer Drug Development: Predicting Mechanism of Action," Science, vol. 258, Oct. 16, 2992, 5 pages.

* cited by examiner

*Primary Examiner* — Andrew D Kosar
*Assistant Examiner* — Karen Cheng
(74) *Attorney, Agent, or Firm* — Alleman Hall McCoy Russell & Tuttle LLP

(57) ABSTRACT

The present application discloses derivatives of ethylene methanedisulfonate as cancer chemotherapeutic agents and methods of synthesizing such derivatives. The derivatives include modifications of ethylene methanedisulfonate by replacing one or both of the chemically most reactive hydrogens of the cyclic sulfonate ester structure. The derivatives of ethylene methanedisulfonate are more active than the parent ester (i.e., ethylene methanedisulfonate) as anticancer agents against a variety of cancers.

7 Claims, No Drawings

DERIVATIVES OF ETHYLENE METHANEDISULFONATE AS CANCER CHEMOTHERAPEUTIC AGENTS

The present application claims priority to U.S. Provisional Patent Application Ser. No. 60/990,561 of Marshall W. Cronyn, entitled DERIVATIVES OF ETHYLENE METHANEDISULFONATE AS CANCER CHEMOTHERAPEUTIC AGENTS, filed Nov. 27, 2007, the disclosure of which is hereby incorporated by reference.

TECHNICAL FIELD

The present application relates to derivatives of ethylene methanedisulfonate, specifically, derivatives of ethylene methanedisulfonate as cancer chemotherapeutic agents.

BACKGROUND

Alkylating agents are a major class of cancer chemotherapeutic compounds. Many clinically used alkylating agents are bifunctional compounds having two chemically reactive centers capable of reacting with and cross-linking biomolecules, such as the opposite strands of duplex DNA. Use of these agents to alkylate biomolecules may lead to a variety of defects in intracellular metabolism, particularly defects in nucleic acid replication and/or transcription, which tend to be more lethal in rapidly growing cancer cells than in normal somatic cells. Busulfan is a bifunctional alkylating agent which is commonly used in the treatment of leukemias. Busulfan is a linear methanesulfonic ester of 1,4-butanediol which functions by forming a butane cross-link between a pair of nucleophiles, such as the 7-position guanine nitrogens in opposite strands of duplex DNA. Initial nucleophilic attack at one of the butane end-carbons in the compound releases a negatively charged methanesulfonic acid group, leaving an uncharged methanesulfonic ester of 1-butanol attached to the nucleophile. A second nucleophilic attack on the opposite butane end-carbon results in cross-linking through the butane moiety, and release of a second negatively charged methanesulfonic acid group. Busulfan is more effective therapeutically than other linear disulfonic esters having cross-linking alkane moieties, which are either shorter or longer than butane.

U.S. Pat. No. 4,950,768 discloses cyclic disulfonic esters having the general structural formula:

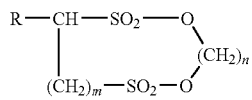

Where m=0 or 1, n=1-5, and R=H, $CH_3$, $CH_3CH_2$ or Cl. These compounds can be used as bifunctional agents for cross-linking a variety of nucleophile-containing biomolecules, such as proteins and nucleic acids. The disclosure includes references that cyclic disulfonic ester in which m=0, n=2 and R=H, (i.e., ethylene methanedisulfonate) is effective in the treatment of a variety of mice cancers, including lymphocytic leukemia, lymphoid leukemia, melanocarcinoma, human breast xenograft and ovarian carcinoma. Cyclic disulfonic esters in which m=0, n=3 or 4 and R=H have also been shown to have anti-leukemia activity.

Unlike uncharged linear alkane disulfonates such as Busulfan, initial nucleo attack on a cyclic diester compound in opening the diester ring, results in a linear sulfonate having a charged sulfonic acid end-group which remains attached to the compound. The charged group has the capacity to affect both the solubility of the compound and its configuration in relation to the alkylated biomolecule, in the period between the two nucleophilic cross-linking reaction events.

The mechanism by which ethylene methane disulfonate alkylates DNA has been studied by Gibson, Hartley and Kohn, Cancer Research, 46, 1679-1683, April 1986. Their work has disclosed that the mechanism of reaction of this alkylating agent is not at all like that of Busulfan and other alkylating agents, which cross-link DNA strands via alkylation of the guanine moiety. Instead, ethylene methanedisulfonate cross-linking appears to occur via phosphate ester alkylation followed by linkage of these strands to protein. This is most likely histones, since the first alkylation step produces a negatively charged intermediate, i.e., $-SO_3-$, and histones, which enfold DNA, are positively charged.

SUMMARY

The present application discloses derivatives of ethylene methanedisulfonate as cancer chemotherapeutic agents and methods of synthesizing such derivatives. The derivatives include modifications of ethylene methanedisulfonate by replacing one or both of the chemically most reactive hydrogens of the cyclic sulfonate ester structure. The derivatives of ethylene methanedisulfonate are more active than the parent ester (i.e., ethylene methanedisulfonate) as anticancer agents against a variety of cancers. Some derivatives of ethylene methanedisulfonate or compounds disclosed in the present application can prevent the growth of cancer cells to 30% or less at $10^{-4}$ molar concentration. Some compounds can prevent the growth of cancer cells to $10^{-5}$ molar or less concentration. Further, some compounds show a lethal toxicity toward cancer cells at a level of 50% or more at $10^{-4}$ molar concentration or less.

DETAILED DESCRIPTION

As described above, toxicology have suggested that, of the several cyclic sulfonate esters described in U.S. Pat. No. 4,950,768, the ethylene methanedisulfonate may provide an advantageous platform for modification aimed at effective cancer chemotherapeutic agents. Modifications by replacement of one or both of the chemically most reactive hydrogens of the cyclic sulfonate ester structure are disclosed to result in a desired type of chemical reactivity characteristic of the leukemia-effective sulfonate ester Busulfan.

In U.S. Pat. No. 4,950,768 the mechanism of action of ethylene methanedisulfonate in the alkylation of the nuclear chromatin of cancer cells during mitosis was described and subsequently the mechanism was confirmed by the study of Gibson, Hartley and Kohn (1).

The present disclosure describes derivatives of ethylene methanedisulfonate which are potential candidates for cancer chemotherapy. As described in more detail below, the derivates examined were obtained in syntheses starting with ethylene methanedisulfonate and replacing one or both of this compound's active hydrogens by variations in $R^1$ and $R^2$:

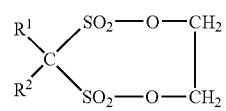

In addition to a disclosure of those structural characteristics which distinguish between the active and inactive anticancer candidates, the present invention reveals structures which are considerably more active than the parent ester, ethylene methanedisulfonate. These compounds fall into two major groups in their anticancer activity. In the first group, at concentration of $10^{-4}$ molar, tumor cells are suppressed in their growth to 30% or less, with some compounds being lethal for up to about 50% of such cells. The compounds in the second group are active against tumor cells at lower concentrations (e.g., $10^{-5}$ to $10^{-8}$ molar) and include those compounds which are toxic to about 60% to 100% of such cells.

Reagents which require a lower concentration for their anticancer effectiveness are expected to be less of a threat toward normal cells in a biological system. The high toxicity toward certain types of cancer cells suggests that, in addition to the usual modes of administration, such as but not limited to, aqueous drip, water drip, i.v. saline drip, i.v. isotonic saline drip or colloidal suspension, these compounds might well be appropriate for topical therapeutic application, perhaps replacing radiation in some cases. As such, the disclosed compounds may be prepared for use by one skilled in the art into a topical and/or extradermal application.

The following outlines the disclosure below. The structures of derivatives of ethylene methanedisulfonate that are active in anticancer activity are disclosed in Section I. Some derivatives are categorized based on their improved solubility compared to their parent compound, i.e., ethylene methanedisulfonate while other derivatives are categorized based on their increased lipophilicity compared to their parent compound. Furthermore, some derivatives are categorized based on their halogenation potential. Still, some derivatives are categorized based on their combined quinone moiety characteristic and alkylating moiety. Section II discloses anticancer activity of derivatives of ethylene methanedisulfonate. Section III discloses syntheses of derivatives of ethylene methanedisulfonate.

Section I. The Structures of Derivatives of Ethylene Methanedisulfonate

The derivatives of ethylene methanedisulfonate are listed in tables below. For some derivatives of ethylene methanedisulfonate, the anticancer activity may be enhanced by the derivatives' improved water solubility compared to their parent compound. For some derivatives, the anticancer activity of derivatives may be enhanced by the derivatives' increased lipophilicity compared to their parent compound. In some examples, the derivatives are more active in anticancer effectiveness because of their potential for halogenation. In other examples, the derivatives are more active anticancer agents because the derivatives possess the combination of the quinone moiety characteristic of mitomycins (antitumor agents) and the alkylating moiety of Busulfan. Thus, derivatives with similar characteristics are grouped in one category and are presented in tables 1, 2, 3, and 4. Some derivatives do not fall into the specific categories of tables 1, 2, 3, and 4. However, these derivatives have anticancer activities for various cancers. These derivatives are disclosed in table 5. Additionally, table 6 discloses compounds that may be used as cancer cell stimulators as well as cancer cell growth inhibitors. It should be noted that some compounds may fall into more than one category. For each compound, the table lists its MWC numbers that are used in the examples of syntheses and NSC numbers that are used in the National Cancer Institute (NCI) screen for cancer therapeutic agents.

Table 1 presents derivatives of ethylene methanedisulfonate that exhibit anticancer activity as shown by the experiment data in Section II. The improved anticancer activity of these derivatives compared to their patent compound may be at least partially due to their improved water solubility.

TABLE 1A

Derivatives of ethylene methanedisulfonate with improved water solubility compared to ethylene methanedisulfonate.

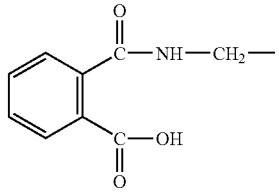

| MWC number | NSC number | R¹ | R² |
|---|---|---|---|
| 94-5 | 671537 | H— | 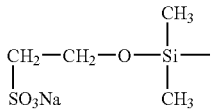 |
| 94-6 | 674991 | H— | 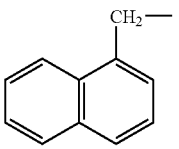 |
| 94-7 | 674992 | CH₂— (naphthyl) | 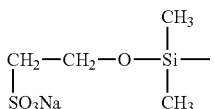 |

TABLE 1A-continued
Derivatives of ethylene methanedisulfonate with improved water solubility compared to ethylene methanedisulfonate.
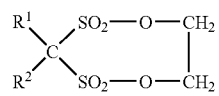
| MWC number | NSC number | R¹ | R² |
|---|---|---|---|
| 94-9 | 674994 | H— | CH₂—CH₂—CH₂—<br>\|<br>O<br>\|<br>SO₃Na |
| 95-3 | 679044 | Na⁺ | naphthalen-1-yl-SO₂— |
| 96-13 | | Br— | CH₂—CH₂—SO₂—<br>\|<br>SO₃Na |
| 96-14 | 693879 | CH₂—CH₂—<br>\|<br>O<br>\|<br>SO₃Na | 2-methylnaphthalen-1-ylmethyl— |
| 96-16 | 693880 | H— | 2-(SO₃H)phenyl-C(=O)— |
| 97-4 | 698122 | Na⁺ | quinolin-8-yl-SO₂— |

TABLE 1B

Derivatives of ethylene methanedisulfonate with improved water solubility compared to ethylene methanedisulfonate.

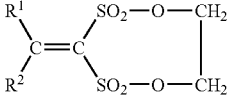

| MWC number | NSC number | R¹ | R² |
|---|---|---|---|
| 95-8 | | 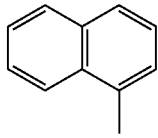 | 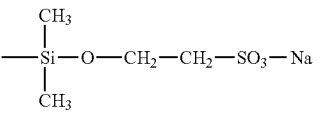 |
| 97-5 | 698123 | 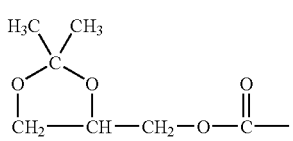 | —ONa |
| 97-9 | 701691 | H— | —OCH$_3$ |
| 05-2 | 737275 | 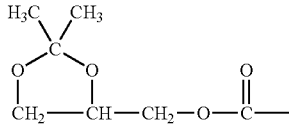 | 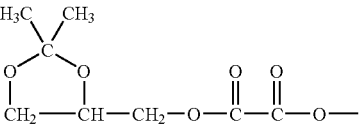 |

TABLE 1C

Derivative of ethylene methanedisulfonate with improved water solubility compared to ethylene methanedisulfonate.

| MWC number | NSC number | Structure |
|---|---|---|
| 96-3 | 686564 | 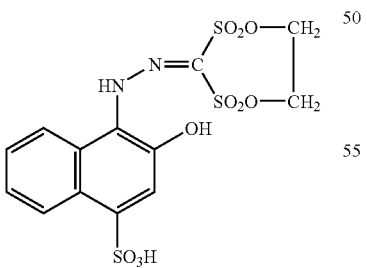 |

Table 2 present derivatives of ethylene methanedisulfonate that exhibit anticancer activity as shown by the experiment data in Section II. The improved anticancer activity of these derivatives compared to their parent compound may be at Least partially due to their increased lipophilicity.

TABLE 2A
Derivatives of ethylene methanedisulfonate with increased lipophilicity compared to ethylene methanedisulfonate.
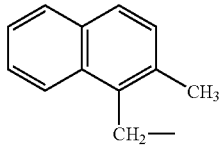
| MWC number | NSC number | R¹ | R² |
|---|---|---|---|
| 96-8 | 693873 | 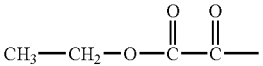 | 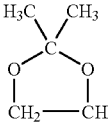 |
| 05-3 | 737276 |  | 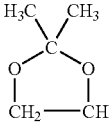 |
| 05-4 | 737277 |  | 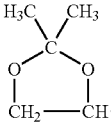 |
| 05-5 | 737278 |  | 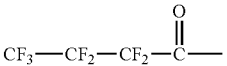 |
| 00-8 | 720683 | 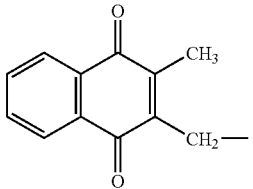 |  |

TABLE 2B

Derivatives of ethylene methanedisulfonate with increased lipophilicity compared to ethylene methanedisulfonate.

$$R^1R^2C=C(SO_2-O-CH_2-CH_2-O-SO_2)$$

| MWC number | NSC number | R¹ | R² |
|---|---|---|---|
| 97-5 | 698123 | (CH₃)₂C(O-CH₂-CH(-)-CH₂-O-C(=O)-)O (2,2-dimethyl-1,3-dioxolan-4-ylmethyl ester) | —ONa |
| 05-2 | 737275 | (CH₃)₂C(O-CH₂-CH(-)-CH₂-O-C(=O)-)O | (CH₃)₂C(O-CH₂-CH(-)-CH₂-O-C(=O)-C(=O)-O-) |

TABLE 3

Derivatives of ethylene methanedisulfonate with potential for halogenation $$R^1R^2C(SO_2-O-CH_2-CH_2-O-SO_2)$$

| MWC number | NSC number | R¹ | R² |
|---|---|---|---|
| 91-4 | 648304 | Br— | Br— |
| 91-5 | 648305 | H— | Br— |
| 91-7 | 648307 | Cl— | Cl— |
| 91-8 | 648308 | I— | I— |
| 91-9 | 648309 | H— | I— |
| 93-2 | 665942 | H— | F— |
| 93-3 | 665943 | F— | Br— |
| 94-1 | 671533 | F— | C₆H₅—CH₂— (benzyl) |
| 95-5 | 679046 | I— | 2-naphthyl-C(=O)— |
| 95-7 | NA | Br— | 1-naphthyl-C(=O)— |
| 96-13 | NA | Br— | —CH(SO₃Na)—CH₂—SO₂— |

TABLE 4
Derivatives of ethylene methanedisulfonate with the combination of the quinone moiety characteristic with alkylating moiety characteristic
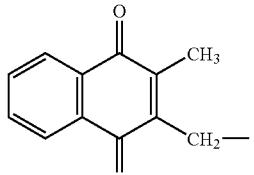
| MWC number | NSC number | R¹ | R² |
|---|---|---|---|
| 96-9 | 693874 | H— | 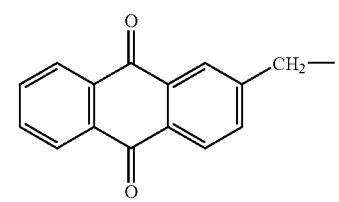 |
| 96-10 | 693875 | H— | 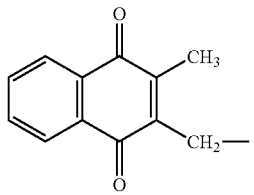 |
| 97-6 | 698124 | CH₃CH₂—O—CH₂— | 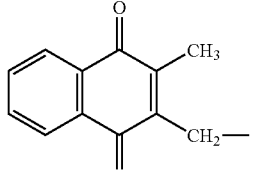 |
| 97-7 | 701690 | $CH_3-\overset{O}{\underset{\parallel}{C}}-$ | 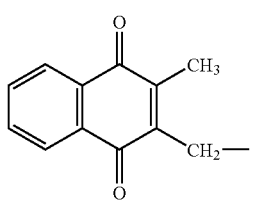 |
| 00-7 | 720682 | CF₃SO₂— | 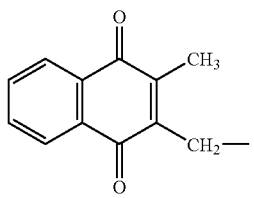 |
| 00-8 | 720683 | $CF_3-CF_2-CF_2-\overset{O}{\underset{\parallel}{C}}-$ | 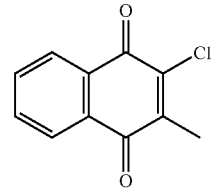 |
| 03-1 | 731260 | H— |  |

TABLE 4-continued

Derivatives of ethylene methanedisulfonate with the combination of the quinone moiety characteristic with alkylating moiety characteristic

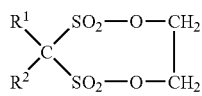

| MWC number | NSC number | R¹ | R² |
|---|---|---|---|
| 03-3 | 731262 | Cl—CH₂—C(=O)— | 2-methyl-3-(CH₂—)-1,4-naphthoquinone |
| 03-6 | 731263 | CH₃—CH=CH—C(=O)— | 2-(CH₂—)-anthraquinone |
| 03-7 | 731264 | CH₃—CH=CH—C(=O)— | 2-chloro-3-methyl-1,4-naphthoquinone |
| 03-8 | 731265 | CH₃—CH=CH—C(=O)— | 2-methyl-3-(CH₂—)-1,4-naphthoquinone |
| 05-3 | 737276 | 2-(CH₂—)-anthraquinone | acetonide-glycerol-O-C(=O)—C(=O)— |
| 05-4 | 737277 | 2-methyl-3-(CH₂—)-1,4-naphthoquinone | acetonide-glycerol-O-C(=O)—C(=O)— |

TABLE 4-continued

Derivatives of ethylene methanedisulfonate with the combination of the quinone moiety characteristic with alkylating moiety characteristic $$\begin{array}{c} R^1 \\ R^2 \end{array} C \begin{array}{c} SO_2-O-CH_2 \\ SO_2-O-CH_2 \end{array}$$

| MWC number | NSC number | R¹ | R² |
|---|---|---|---|
| 05-5 | 737278 | 2-chloro-3-methyl-1,4-naphthoquinone | (dimethyl dioxolane)-CH₂-O-C(O)-C(O)- |

TABLE 5

Derivatives of ethylene methanedisulfonate that are cancer cell stimulators and cancer cell inhibitors.

$$\begin{array}{c} R^1 \\ R^2 \end{array} C \begin{array}{c} SO_2-O-CH_2 \\ SO_2-O-CH_2 \end{array}$$

| MWC number | NSC number | R¹ | R² |
|---|---|---|---|
| 94-4 | 671536 | H— | phthalimido-CH₂— |
| 94-5 | 671537 | H— | 2-(HOOC)C₆H₄-C(O)-NH-CH₂— |

TABLE 5-continued

Derivatives of ethylene methanedisulfonate that are cancer cell stimulators and cancer cell inhibitors.

$$\begin{array}{c} R^1 \\ R^2 \end{array} C \begin{array}{c} SO_2-O-CH_2 \\ SO_2-O-CH_2 \end{array}$$

| MWC number | NSC number | R¹ | R² |
|---|---|---|---|
| 90-1 | 372239 | H— | $CH_3$— |
| 93-2 | 665942 | H— | F— |
| 94-3 | 671535 | H— | $CH_3(CH_2)_6CH_2$—O—$CH_2$— |
| 00-10 | 720685 | H— | 3,5,6-trichloro-2-methylpyrazinyl |

TABLE 6A

Derivatives of ethylene methanedisulfonate that are not grouped in a common characteristic.

$$\begin{array}{c} R^1 \\ R^2 \end{array} C \begin{array}{c} SO_2-O-CH_2 \\ SO_2-O-CH_2 \end{array}$$

| MWC number | NSC number | R¹ | R² |
|---|---|---|---|
| 90-3 | 634863 | H— | $C_6H_5$-$CH_2$— |
| 91-3 | 648303 | H— | 4-$CH_3$-$C_6H_4$-$SO_2$-NH-C(O)— |
| 93-1 | 665941 | —$CH_2CH_2CN$ | —$CH_2CH_2CN$ |

TABLE 6A-continued
Derivatives of ethylene methanedisulfonate that are not grouped in a common characteristic.
$$\begin{array}{c} R^1 \diagdown \phantom{C} \diagup SO_2-O-CH_2 \\ C \\ R^2 \diagup \phantom{C} \diagdown SO_2-O-CH_2 \end{array}$$
| MWC number | NSC number | R¹ | R² |
|---|---|---|---|
| 94-2 | 671534 | H— | 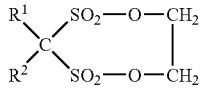 |
| 94-8 | 674993 | $CH_3-\overset{O}{\underset{\phantom{x}}{C}}-$ | 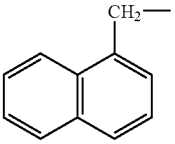 |
| 95-1 | 679042 | H— | 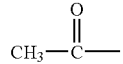 |
| 95-2 | 679043 | H— | 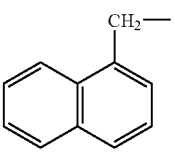 |
| 95-4 | NA | H— | 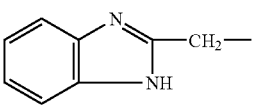 |
| 95-6 | 679047 | H— | 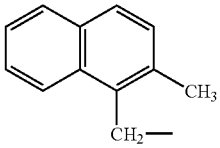 |
| 96-1 | 686562 | H— | 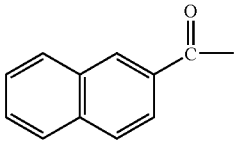 |
| 97-2 | 698120 | CH₃CH₂—O—CH₂— | CH₃CH₂—O—CH₂— |

TABLE 6B

Derivatives of ethylene methanedisulfonate that are not grouped in a common characteristic.

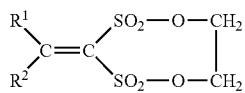

| MWC number | NSC number | R$^1$ | R$^2$ |
|---|---|---|---|
| 97-3 | 698121 | CH$_3$— | CH$_3$—C(=O)—O— |

Section II. Anticancer Activity of Derivatives of Ethylene Methanedisulfonate

The compounds listed in Section II are arranged by their NSC number followed by the percent of growth of human tumor cells when the compound is administrated at $10^{-4}$ molar concentration.

In section III are listed compounds with activity against human tumor cells at concentrations of $10^{-5}$ molar or less down to $10^{-8}$ molar. Also included in this section are compounds with lethal activity toward human cancer cells of about 50% to 100%. The high toxicity toward certain types of cancer cells may indicate additional therapeutic application of these compounds besides the usual administration mode (e.g., drip of water solution or colloidal suspension). For example, Section III compounds may be appropriate for topical therapeutic application, which may replace radiation in some cases.

In the NCI screening process, each compound was tested and described by a minimum of 60 data points. The test data include, but are not limited to the type of cancer, the molar concentration used in the screen, and the percent growth of the cancer. In some cases, NMR and elemental analysis were used for structural assignment.

SECTION II
$10^{-4}$ molar, 30% growth or less

Leukemia

CCRF-CEM

| NSC | % |
|---|---|
| 348948 | −3 |
| 372239 | −6 |
| 648307 | 29 |
| 665941 | 5 |
| 671534 | −43 |
| 674993 | 5 |
| 679042 | 15 |
| 686562 | −3 |
| 686564 | 14 |
| 693873 | 5 |
| 701691 | 24 |
| 720682 | −5 |
| 720683 | 5 |
| 731262 | 18 |
| 731263 | 15 |
| 737276 | −38 |
| 737278 | 22 |

HL-60 (TB)

| NSC | % |
|---|---|
| 634863 | −32 |
| 648308 | −16 |
| 665941 | −17 |
| 674042 | −5 |
| 674991 | 15 |
| 674993 | −44 |
| 686562 | −20 |
| 693875 | 4 |
| 720682 | −22 |
| 731260 | 13 |
| 731264 | 17 |
| 731265 | 2 |
| 737276 | −3 |
| 737277 | −33 |
| 737278 | −25 |

K562

| NSC | % |
|---|---|
| 348948 | 5 |
| 372239 | 12 |
| 648308 | −16 |
| 674992 | 3 |
| 674993 | 0 |
| 679042 | 14 |
| 679044 | 15 |
| 686562 | 16 |
| 693873 | 19 |
| 698874 | −28 |
| 720682 | −11 |
| 731260 | 20 |
| 731262 | 18 |
| 731263 | 12 |
| 731264 | 19 |
| 731265 | 11 |
| 737276 | 29 |
| 737277 | 5 |
| 737278 | 12 |

MOLT-4

| NSC | % |
|---|---|
| 348948 | 5 |
| 372239 | 12 |
| 634863 | 5 |
| 634992 | 3 |
| 648308 | −22 |
| 665941 | 6 |
| 671534 | −20 |
| 679042 | −3 |
| 686562 | −32 |
| 686564 | 23 |
| 693873 | 11 |
| 693874 | −51 |
| 693879 | −16 |
| 698120 | 23 |
| 720682 | −11 |
| 720685 | 24 |
| 731265 | 2 |
| 737276 | −26 |
| 737277 | −12 |

RPMI-8226

| NSC | % |
|---|---|
| 634863 | −14 |
| 648307 | 21 |
| 665941 | 24 |
| 671534 | −10 |
| 674992 | −25 |
| 674993 | −42 |
| 679042 | −42 |
| 686562 | 9 |
| 693873 | −29 |
| 693875 | 14 |
| 693879 | −28 |
| 698120 | 10 |
| 701690 | −18 |
| 720682 | −4 |
| 720683 | 28 |
| 731260 | −36 |
| 731262 | −57 |
| 731263 | −7 |
| 731264 | −18 |
| 731265 | −40 |
| 737276 | −35 |

SECTION II
$10^{-4}$ molar, 30% growth or less

SR

| | |
|---|---|
| 634863 | 9 |
| 665941 | 10 |
| 671534 | −23 |
| 671535 | 5 |
| 671536 | 15 |
| 674991 | 20 |
| 674992 | 10 |
| 674993 | −47 |
| 679042 | 12 |
| 693873 | 10 |
| 720683 | −22 |
| 731260 | 15 |
| 731262 | 16 |
| 731263 | 24 |
| 731264 | 7 |
| 737275 | 7 |
| 737276 | 12 |

Non-Small Cell Lung

AS49/ATCC

| | |
|---|---|
| 648308 | −17 |
| 671534 | 14 |
| 686562 | 30 |
| 720682 | −37 |
| 720683 | −45 |
| 731264 | −36 |
| 731268 | −47 |

EKVX

| | |
|---|---|
| 634863 | 10 |
| 648308 | −35 |
| 671534 | −11 |
| 693875 | −23 |
| 698122 | 28 |
| 720682 | −36 |
| 731265 | −57 |

HOP-62

| | |
|---|---|
| 670993 | −53 |
| 671534 | −49 |
| 674992 | −48 |
| 679042 | 9 |
| 686562 | 5 |
| 693875 | 16 |
| 698120 | 23 |
| 720683 | −28 |
| 731260 | −56 |
| 731262 | −51 |
| 731263 | −38 |
| 731264 | −56 |

HOP-18

| | |
|---|---|
| 731265 | −43 |

HOP-92

| | |
|---|---|
| 348948 | 6 |
| 671534 | −25 |
| 674991 | 22 |
| 674992 | −23 |
| 674993 | −33 |
| 693873 | 19 |
| 693875 | 28 |
| 693879 | −35 |
| 698124 | 27 |
| 731260 | −3 |
| 731262 | −7 |
| 731263 | −16 |
| 731265 | −43 |
| 732264 | 22 |
| 737276 | −47 |

NCI-H226

| | |
|---|---|
| 634863 | 21 |
| 648307 | 23 |
| 648309 | 20 |
| 674992 | −46 |
| 693875 | −43 |
| 698120 | 0 |
| 720682 | −45 |
| 731262 | 6 |
| 731263 | 10 |
| 731265 | −4 |
| 737276 | 10 |

NCI-H522

| | |
|---|---|
| 634863 | 23 |
| 648308 | −45 |
| 665941 | 18 |
| 671534 | −40 |
| 674993 | −47 |
| 686562 | −19 |
| 693875 | −63 |
| 698122 | −40 |
| 698124 | −45 |
| 720685 | −22 |
| 737278 | −30 |

NCI-H460

| | |
|---|---|
| 348948 | 6 |
| 372239 | 2 |
| 634863 | 11 |
| 674991 | 22 |
| 674992 | −67 |
| 679042 | 14 |
| 686564 | 6 |
| 693873 | 8 |
| 693875 | −17 |
| 693879 | −58 |
| 693880 | −11 |
| 698120 | −38 |
| 698121 | 12 |
| 698122 | −40 |
| 698124 | 11 |
| 720682 | −59 |
| 731260 | 4 |
| 731263 | 2 |
| 731264 | 10 |
| 731265 | 5 |
| 733275 | 13 |
| 737276 | −59 |

NCI-H322M

| | |
|---|---|
| 648308 | −45 |
| 671534 | −42 |
| 674992 | −42 |
| 674993 | −47 |
| 693873 | −13 |
| 693875 | −46 |
| 693879 | −71 |
| 698120 | 20 |
| 720683 | 25 |

NCI-H23

| | |
|---|---|
| 634863 | 21 |
| 665941 | 25 |
| 671534 | −12 |
| 674992 | −2 |
| 674993 | −26 |
| 679042 | 16 |
| 693873 | 20 |
| 693880 | 12 |
| 698122 | 27 |
| 698124 | 16 |
| 731260 | −54 |
| 731262 | −6 |
| 731263 | 31 |

SECTION II
$10^{-4}$ molar, 30% growth or less

HCC-2998

| | |
|---|---:|
| 634863 | −48 |
| 698122 | −12 |
| 698124 | 8 |
| 737275 | −12 |

Colon Cancer

COLO205

| | |
|---|---:|
| 693880 | 5 |
| 698124 | −25 |
| 731262 | −10 |
| 731263 | 5 |
| 731264 | 30 |
| 731265 | −50 |
| 737277 | −8 |
| 737278 | −9 |

HCT-116

| | |
|---|---:|
| 634863 | 30 |
| 665941 | 26 |
| 671534 | −42 |
| 679042 | −31 |
| 679044 | −52 |
| 686562 | 0 |
| 693873 | 22 |
| 693875 | −24 |
| 693880 | 20 |
| 698120 | −6 |
| 698122 | 16 |
| 720682 | 19 |
| 720683 | 22 |
| 731264 | 26 |

HCT-15

| | |
|---|---:|
| 665941 | 27 |
| 671534 | −6 |
| 674993 | −57 |
| 679042 | 4 |
| 679043 | −49 |
| 686562 | 15 |
| 693873 | 6 |
| 693875 | −16 |
| 693879 | −39 |
| 698120 | −27 |
| 698122 | 18 |
| 698124 | 15 |
| 720685 | 7 |
| 731260 | 17 |
| 731264 | −59 |
| 737276 | −12 |

HT29

| | |
|---|---:|
| 648308 | −18 |
| 671534 | −16 |
| 686562 | 26 |
| 693873 | 4 |
| 693875 | −16 |
| 698120 | −3 |
| 701690 | −25 |
| 720682 | −43 |
| 731262 | −16 |
| 731263 | 1 |
| 731265 | −6 |
| 737276 | −25 |

KM12

| | |
|---|---:|
| 648308 | −58 |
| 665941 | 27 |
| 686562 | 22 |
| 693875 | −37 |
| 698122 | 7 |
| 720682 | 20 |
| 720683 | 26 |
| 731262 | −26 |
| 731263 | 2 |
| 731265 | −16 |

SW620

| | |
|---|---:|
| 693873 | 30 |
| 698120 | −3 |
| 731260 | 1 |
| 731262 | −39 |
| 731263 | −38 |

CNS Cancer

SF-268

| | |
|---|---:|
| 372239 | 29 |
| 634863 | 24 |
| 648308 | −11 |
| 671534 | −20 |
| 674991 | 11 |
| 674992 | −9 |
| 674993 | −37 |
| 686562 | 29 |
| 693873 | 20 |
| 698120 | 21 |
| 698122 | 24 |
| 698124 | 20 |
| 720682 | 1 |
| 720683 | 1 |
| 731260 | 10 |
| 731262 | −26 |
| 731263 | −24 |
| 731264 | 7 |
| 731265 | −49 |
| 737275 | 24 |
| 737276 | −40 |

SF-295

| | |
|---|---:|
| 648308 | −4 |
| 671534 | 3 |
| 679042 | 0 |
| 686562 | 22 |
| 693873 | 18 |
| 698121 | 24 |
| 698122 | 18 |
| 731260 | −46 |
| 731262 | −54 |
| 731264 | −57 |
| 731265 | −57 |
| 737276 | −12 |

SNB-19

| | |
|---|---:|
| 348948 | 18 |
| 372239 | 26 |
| 674992 | −52 |
| 698120 | 14 |
| 731263 | 10 |
| 737276 | −59 |

XF 498

| | |
|---|---:|
| 648308 | −67 |

SF-539

| | |
|---|---:|
| 372239 | 28 |
| 634863 | −1 |
| 648308 | −25 |
| 665942 | 28 |
| 674991 | 4 |
| 686562 | 10 |
| 693873 | −3 |
| 698120 | 20 |
| 698121 | 18 |
| 698122 | 30 |
| 720685 | 7 |
| 731260 | 1 |
| 731263 | −23 |
| 737275 | 15 |
| 737276 | −43 |

SECTION II
10⁻⁴ molar, 30% growth or less

SNB-75

| | |
|---|---|
| 348948 | 18 |
| 372239 | 28 |
| 634863 | 25 |
| 648308 | −36 |
| 665941 | 28 |
| 671534 | 3 |
| 674991 | −24 |
| 674992 | −23 |
| 674993 | −35 |
| 686564 | 7 |
| 693873 | −1 |
| 698124 | 11 |
| 731264 | −33 |
| 731265 | −26 |

SNB-78

| | |
|---|---|
| 648308 | −6 |

U-251

| | |
|---|---|
| 372239 | 16 |
| 634863 | 10 |
| 665941 | 20 |
| 671534 | −56 |
| 674991 | 9 |
| 674992 | −20 |
| 679042 | 21 |
| 693873 | 2 |
| 693875 | 8 |
| 698120 | −47 |
| 698122 | −53 |
| 698124 | 20 |
| 720682 | −36 |
| 720683 | 12 |
| 731260 | 2 |
| 731264 | −5 |
| 737276 | −53 |

Melanoma

LOXIMVI

| | |
|---|---|
| 634863 | 21 |
| 665941 | 5 |
| 671534 | −30 |
| 674991 | 10 |
| 674992 | −73 |
| 679042 | −50 |
| 679044 | 23 |
| 686562 | −27 |
| 693873 | 7 |
| 698120 | −25 |
| 698122 | −43 |
| 698124 | −55 |
| 731260 | −43 |
| 737276 | −48 |

M14

| | |
|---|---|
| 674992 | −40 |
| 674993 | −32 |
| 679042 | 23 |
| 686562 | 23 |
| 693875 | −3 |
| 693880 | −4 |
| 698120 | −36 |
| 698122 | 10 |
| 720683 | −56 |
| 731260 | −58 |
| 731264 | −6 |
| 737278 | −4 |

MALME-3M

| | |
|---|---|
| 693875 | −35 |
| 693880 | −15 |
| 698122 | 29 |
| 698124 | −9 |
| 737276 | −50 |

SK-MEL-2

| | |
|---|---|
| 665941 | 26 |
| 671543 | 30 |
| 674992 | −43 |
| 679043 | −59 |
| 693873 | −2 |
| 693875 | 8 |
| 698122 | 24 |
| 720682 | −58 |
| 720683 | −57 |
| 731265 | 15 |

SK-MEL-28

| | |
|---|---|
| 648308 | −29 |
| 674993 | −56 |
| 693873 | 29 |
| 693875 | −8 |
| 693879 | −5 |
| 698120 | 12 |
| 731260 | −5 |
| 731263 | −23 |
| 731264 | −59 |
| 737276 | −52 |

SK-MEL-5

| | |
|---|---|
| 679042 | −28 |
| 686562 | 4 |
| 693873 | 23 |
| 698120 | 25 |
| 698122 | 15 |
| 698124 | 9 |
| 731260 | −54 |
| 731261 | −49 |
| 731277 | 19 |
| 737276 | −4 |

UACC-257

| | |
|---|---|
| 648308 | −54 |
| 674992 | −11 |
| 679042 | 12 |
| 686562 | 28 |
| 693873 | 23 |
| 693875 | 14 |
| 693879 | −32 |
| 698120 | −14 |
| 698122 | 13 |
| 698124 | 12 |
| 720683 | −18 |
| 731263 | −20 |

UACC-62

| | |
|---|---|
| 348948 | −13 |
| 372239 | −14 |
| 634863 | 20 |
| 648307 | 7 |
| 648309 | 17 |
| 671534 | −30 |
| 674992 | −48 |
| 686562 | 10 |
| 693873 | −6 |
| 693875 | −16 |
| 698120 | −36 |
| 698122 | −46 |
| 698124 | −32 |
| 701690 | −57 |

-continued

SECTION II
$10^{-4}$ molar, 30% growth or less

| | |
|---|---|
| 731262 | −51 |
| 731263 | 16 |
| 731264 | −16 |
| 731265 | −13 |

Ovarian Cancer

IGROVI

| | |
|---|---|
| 634863 | −3 |
| 648308 | −24 |
| 686562 | 16 |
| 693873 | −29 |
| 693875 | −58 |
| 698120 | −28 |
| 698122 | 17 |
| 698124 | 6 |
| 720682 | −18 |
| 720683 | 27 |
| 731263 | 3 |
| 731265 | 4 |

SK-OV-3

| | |
|---|---|
| 648308 | −49 |
| 665941 | 28 |
| 671534 | −18 |
| 686562 | 25 |
| 720682 | 20 |
| 720683 | 24 |
| 731265 | −61 |

OVCAR-3

| | |
|---|---|
| 634863 | −52 |
| 648308 | −14 |
| 665941 | 12 |
| 671534 | −59 |
| 679049 | 22 |
| 686562 | 25 |
| 693873 | −48 |
| 693880 | 76 |
| 698120 | −13 |
| 698122 | 25 |
| 698124 | −17 |
| 720682 | −42 |
| 720683 | 30 |
| 731260 | 28 |
| 731262 | −48 |
| 731264 | 5 |
| 731265 | 7 |

OVCAR-4

| | |
|---|---|
| 634863 | 22 |
| 648308 | −39 |
| 665941 | 4 |
| 674992 | −35 |
| 686562 | −39 |
| 693873 | −31 |
| 693879 | −40 |
| 698122 | 30 |
| 698124 | 14 |
| 720682 | −23 |
| 731260 | 11 |
| 731262 | −9 |
| 731264 | 19 |

OVCAR-5

| | |
|---|---|
| 634863 | 22 |
| 671534 | −27 |
| 693873 | −22 |
| 698120 | −28 |
| 701690 | −53 |
| 731263 | 20 |

OVCAR-8

| | |
|---|---|
| 648308 | −25 |
| 674993 | −29 |
| 679042 | −33 |

-continued

SECTION II
$10^{-4}$ molar, 30% growth or less

| | |
|---|---|
| 679043 | −53 |
| 686562 | 29 |
| 693873 | 20 |
| 693875 | −39 |
| 693880 | −33 |
| 698120 | −43 |
| 698122 | 19 |
| 731260 | 18 |
| 731262 | 10 |
| 731263 | −39 |
| 731265 | −38 |
| 737276 | 5 |

Renal Cancer

786-0

| | |
|---|---|
| 348948 | 24 |
| 634863 | 12 |
| 665941 | 6 |
| 671534 | −32 |
| 674991 | 16 |
| 679042 | 22 |
| 686562 | 2 |
| 693874 | −16 |
| 693875 | −26 |
| 698120 | 15 |
| 731263 | 1 |
| 737275 | 17 |

ACHN

| | |
|---|---|
| 348948 | 22 |
| 372239 | 20 |
| 634863 | 29 |
| 665941 | 13 |
| 674991 | −10 |
| 674992 | −31 |
| 686562 | 9 |
| 686564 | 26 |
| 693873 | 27 |
| 693880 | 8 |
| 698120 | 18 |
| 698121 | 29 |
| 720683 | −27 |
| 731260 | −12 |

RXF-393

| | |
|---|---|
| 665941 | 23 |
| 671534 | −21 |
| 679049 | 23 |
| 686562 | 25 |
| 693873 | −16 |
| 693875 | 7 |
| 698120 | −36 |
| 720682 | 24 |
| 720683 | 9 |
| 731260 | 28 |
| 731262 | −59 |
| 731263 | −45 |
| 731264 | −50 |
| 731265 | −15 |
| 737276 | −54 |

RXF-631

| | |
|---|---|
| 648308 | −44 |

TK-10

| | |
|---|---|
| 648308 | −19 |
| 671534 | 18 |
| 674992 | −38 |
| 693879 | −3 |
| 701690 | −8 |
| 731265 | −10 |

SN12C

| | |
|---|---|
| 648308 | −61 |
| 665941 | 15 |

SECTION II
$10^{-4}$ molar, 30% growth or less

| | |
|---|---|
| 671534 | −21 |
| 674992 | −54 |
| 679042 | 8 |
| 686562 | 28 |
| 693873 | 21 |
| 693875 | 11 |
| 693879 | −57 |
| 698120 | 24 |
| 698122 | 28 |
| 698124 | −25 |
| 720682 | −70 |
| 720683 | −37 |
| 731260 | −12 |
| 731262 | −30 |
| 731263 | −53 |
| 731265 | −17 |

CAKI-1

| | |
|---|---|
| 348948 | −6 |
| 372239 | 20 |
| 648307 | 23 |
| 665941 | 28 |
| 671534 | 12 |
| 674991 | −8 |
| 679042 | −2 |
| 686562 | −1 |
| 693873 | 26 |
| 693875 | −11 |
| 693880 | −8 |
| 698120 | 7 |
| 701690 | −53 |
| 720682 | 16 |
| 731260 | 18 |
| 731265 | −2 |
| 737276 | 15 |

UO-31

| | |
|---|---|
| 671534 | −48 |
| 674991 | 29 |
| 686562 | −3 |
| 693873 | 27 |
| 693875 | −38 |
| 693879 | −48 |
| 720682 | 29 |
| 731260 | 30 |
| 731262 | 9 |
| 731263 | 1 |
| 731264 | 12 |
| 731265 | −10 |
| 737277 | 22 |
| 737278 | 4 |

Prostate Cancer

PC-3

| | |
|---|---|
| 671534 | 8 |
| 674992 | −45 |
| 679044 | 23 |
| 693873 | 8 |
| 693875 | 8 |
| 693880 | 5 |
| 731260 | 9 |
| 731263 | 11 |

DU-145

| | |
|---|---|
| 674993 | −52 |
| 686562 | 9 |
| 693873 | −1 |
| 693875 | −2 |
| 698120 | 24 |
| 698122 | 2 |
| 698124 | 27 |
| 731260 | 12 |
| 731263 | 1 |
| 737278 | 6 |

Breast Cancer

MCF 7

| | |
|---|---|
| 665941 | 18 |
| 671534 | −51 |
| 674991 | 22 |
| 679042 | 6 |
| 686562 | 23 |
| 693873 | 14 |
| 693880 | −1 |
| 698120 | 27 |
| 698122 | 12 |
| 698124 | 19 |
| 720682 | 1 |
| 720683 | −24 |
| 731260 | 6 |
| 731263 | −17 |
| 731265 | −8 |
| 737276 | −59 |

MCF7/ADR-RES

| | |
|---|---|
| 671534 | −30 |
| 674991 | 20 |
| 674992 | 6 |
| 679042 | 15 |
| 679043 | −12 |
| 686562 | −7 |
| 693873 | 5 |
| 693874 | −41 |
| 693875 | −22 |
| 693880 | 4 |
| 698120 | −26 |
| 698122 | −5 |
| 698124 | 30 |
| 701690 | −40 |
| 720682 | 1 |
| 731260 | 25 |
| 731262 | 25 |
| 731263 | 11 |
| 731264 | 20 |
| 737276 | −29 |

BT-549

| | |
|---|---|
| 665941 | 18 |
| 674991 | 11 |
| 693873 | 30 |
| 693879 | −34 |
| 698120 | −4 |
| 698124 | 27 |
| 720683 | −50 |
| 731260 | −32 |
| 731263 | −20 |
| 731264 | −52 |
| 731265 | −54 |
| 737276 | −49 |

HS 578T

| | |
|---|---|
| 665941 | −8 |
| 671534 | 8 |
| 674992 | −2 |
| 686562 | 24 |
| 693873 | 8 |
| 693874 | −21 |
| 693875 | 4 |
| 698120 | 15 |
| 698124 | 27 |
| 720683 | −14 |
| 731260 | 8 |
| 731262 | −3 |
| 731263 | −18 |
| 731264 | −12 |
| 731265 | −18 |
| 737276 | 17 |
| 737277 | 24 |

SECTION II
$10^{-4}$ molar, 30% growth or less

| | |
|---|---|
| MDA-MB-231/ATCC | |
| 671534 | −54 |
| 674992 | −48 |
| 679042 | 30 |
| 679043 | −12 |
| 693874 | −22 |
| 693875 | 1 |
| 693879 | −54 |
| 693880 | 25 |
| 698120 | 18 |
| 698122 | 26 |
| 731260 | −15 |
| 731263 | −33 |
| 737276 | −9 |
| T-47D | |
| 665941 | 25 |
| 671534 | 2 |
| 674991 | 18 |
| 674993 | −49 |
| 693875 | −19 |
| 701690 | −54 |
| 737276 | −39 |
| MDA-MB-435 | |
| 674992 | −51 |
| 679042 | 23 |
| 693873 | −10 |
| 693875 | −27 |
| 698120 | 1 |
| 698122 | 19 |
| 737277 | −11 |
| 737278 | −45 |
| MDA-N | |
| 671534 | −25 |
| 674992 | −51 |
| 679042 | 3 |
| 686562 | 17 |
| 693873 | −60 |
| 693874 | −59 |
| 693875 | −15 |
| 698120 | 3 |
| 698122 | 10 |

Small Cell Lung Cancer

| | |
|---|---|
| DMS114 | |
| 648308 | −46 |
| DMS273 | |
| 648308 | −45 |

Section III

| Tumor type | NSC # | Molar Concentration | | | | |
|---|---|---|---|---|---|---|
| | | $10^{-4}$ | $10^{-5}$ | $10^{-6}$ | $10^{-7}$ | $10^{-8}$ |
| | | % Growth | | | | |
| Leukemia | | | | | | |
| CCRF-CEM | 679043 | −49 | 37 | | | |
| | 648308 | −44 | 55 | | | |
| | 693874 | −49 | 28 | | | |
| | 693875 | −61 | 18 | | | |
| | 693879 | −33 | 52 | | | |
| | 698121 | 18 | 51 | 61 | 68 | |
| | 698123 | 32 | 58 | 57 | | |
| | 701690 | −73 | 55 | | | |
| HL-60(TB) | 671534 | −64 | 58 | | | |
| | 679043 | −49 | −33 | | | |
| MOLT-4 | 679043 | −46 | 36 | | | |
| | 693875 | −44 | 16 | | | |
| | 698121 | (85) | 46 | | | |
| | 737278 | −41 | 53 | | | |
| RPMI-8226 | 648308 | −37 | 48 | | | |
| | 679043 | −54 | 56 | | | |
| | 693874 | −55 | | | | |
| K562 | 679043 | −42 | 48 | | | |
| | 671534 | −51 | | | | |
| | 698121 | 54 | 59 | 54 | 52 | |
| | 698123 | 63 | 41 | | | |
| | 701690 | −66 | | | | |
| SR | 648308 | −37 | 48 | | | |
| | 679043 | −63 | 42 | | | |
| | 693874 | −45 | −15 | 9 | 48 | 79 |
| | 693875 | −19 | 13 | | | |
| | 698121 | 60 | 31 | | | |
| | 701690 | −100 | −8 | 19 | | |
| | 701691 | 12 | 49 | | | |
| | 720682 | −14 | 30 | | | |
| | 731265 | 12 | 15 | 57 | | |
| | 737278 | −37 | 20 | 33 | 56 | |
| | 737277 | −25 | 50 | | | |
| Non-Small Cell Lung Cancer | | | | | | |
| A549/ATCC | 693879 | −62 | | | | |
| | 679043 | −77 | | | | |
| | 693874 | −93 | | | | |
| | 693875 | −30 | 53 | | | |
| | 701690 | −97 | | | | |
| EKVX | 693880 | 25 | 6 | | | |
| | 648303 | 59 | 66 | 69 | 67 | 57 |
| | 648304 | 51 | 57 | 58 | 62 | 58 |
| | 648305 | 51 | 56 | 59 | 60 | 65 |
| | 674992 | −94 | | | | |
| | 674993 | −98 | | | | |
| | 679043 | −98 | | | | |
| | 698120 | −99 | | | | |
| | 693874 | −93 | | | | |
| | 693879 | −90 | | | | |
| | 701690 | −91 | | | | |
| | 731262 | −61 | | | | |
| | 737276 | −81 | | | | |
| HOP-62 | 648308 | −69 | | | | |
| | 737277 | −84 | | | | |
| | 665941 | 16 | 46 | 48 | 25 | 25 |
| | 679043 | −77 | | | | |
| | 693874 | −94 | | | | |
| | 701690 | −92 | 52 | | | |
| | 720682 | −96 | | | | |
| | 731265 | −80 | 49 | | | |
| | 737276 | −84 | | | | |
| | 693879 | −65 | | | | |
| HOP-18 | 648303 | 69 | 43 | 39 | 33 | 31 |
| | 648304 | 53 | 75 | 52 | 14 | 42 |
| | 648305 | −61 | 68 | 49 | 63 | 63 |
| | 679042 | 18 | 41 | 29 | 51 | 58 |
| | 701691 | 44 | 56 | 92 | 71 | 58 |
| NCI-H23 | 648308 | −70 | 56 | | | |
| | 679043 | −48 | 75 | | | |
| | 693875 | 10 | 51 | | | |
| | 693879 | −65 | | | | |
| | 698120 | −72 | | | | |
| | 693874 | −89 | 62 | | | |
| | 701690 | −91 | | | | |
| | 720682 | −68 | | | | |
| | 720683 | −75 | | | | |
| | 731264 | −72 | | | | |
| | 731265 | −74 | | | | |
| | 737276 | −75 | | | | |

-continued

Section III

| Tumor type | NSC # | 10⁻⁴ | 10⁻⁵ | 10⁻⁶ | 10⁻⁷ | 10⁻⁸ |
|---|---|---|---|---|---|---|
| | | | | % Growth | | |
| LXFL529 | 648308 | −72 | 55 | | | |
| HOP-92 | 648308 | −78 | | | | |
| | 679042 | 18 | 41 | 29 | 51 | 56 |
| | 693874 | −88 | | | | |
| | 701690 | −66 | 23 | 60 | | |
| | 701691 | 44 | 56 | 92 | 71 | 58 |
| NCI-H226 | 648303 | 16 | 37 | 51 | 55 | 53 |
| | 648304 | −1 | 49 | 47 | 54 | 62 |
| | 648305 | 7 | 16 | 20 | 21 | 43 |
| | 648308 | −91 | | | | |
| | 671534 | −36 | 45 | | | |
| | 674993 | −70 | | | | |
| | 679043 | −63 | 49 | | | |
| | 693874 | −82 | 48 | | | |
| | 720683 | −68 | | | | |
| NCI-H460 | 671534 | −71 | | | | |
| | 686562 | −50 | 56 | | | |
| | 674993 | −80 | | | | |
| | 693874 | −73 | 59 | | | |
| | 701690 | −100 | 42 | | | |
| NCI-H522 | 674992 | −75 | | | | |
| | 693874 | −69 | | | | |
| | 693879 | −100 | 35 | 63 | | |
| | 698120 | −83 | | | | |
| | 701690 | −100 | 35 | 57 | 77 | 67 |
| | 701691 | 66 | 44 | 67 | 48 | 73 |
| | 720682 | −72 | | | | |
| | 720683 | −68 | | | | |
| | 737276 | −91 | | | | |
| NCI-H322M | 693874 | −100 | | | | |
| | 693879 | −71 | | | | |
| | 701690 | −100 | | | | |
| | 720682 | −97 | | | | |
| | 731265 | −80 | | | | |
| | 731262 | −82 | | | | |
| | 737276 | −87 | | | | |
| Colon Cancer | | | | | | |
| HCT-15 | 693880 | −41 | 40 | | | |
| | 701690 | −100 | | | | |
| | 720682 | −72 | | | | |
| | 731262 | −64 | | | | |
| | 731263 | −65 | | | | |
| COLO205 | 634863 | −87 | | | | |
| | 648308 | −61 | | | | |
| | 671534 | −83 | | | | |
| | 674992 | −96 | | | | |
| | 674993 | −100 | | | | |
| | 679043 | −98 | −27 | | | |
| | 693873 | −83 | | | | |
| | 693875 | −62 | | | | |
| | 693879 | −73 | 57 | | | |
| | 701690 | −100 | 60 | 58 | | |
| | 720682 | −88 | | | | |
| | 720683 | −84 | | | | |
| | 737276 | −96 | | | | |
| HCT-116 | 648308 | −100 | | | | |
| | 674992 | −66 | | | | |
| | 674993 | −61 | | | | |
| | 679043 | −99 | 15 | | | |
| | 693879 | −79 | | | | |
| | 701690 | −100 | | | | |
| | 731263 | −100 | | | | |
| | 731260 | −89 | | | | |
| | 731265 | −100 | | | | |
| | 737276 | −86 | | | | |
| HT-29 | 698122 | −64 | | | | |
| | 674993 | −64 | | | | |
| | 679043 | −95 | 57 | | | |
| | 693879 | −86 | | | | |
| | 720683 | −100 | −37 | −6 | 23 | |
| KM12 | 671536 | 50 | 42 | 39 | 59 | 40 |
| | 674992 | −85 | | | | |
| | 671537 | 62 | 54 | 45 | 61 | 41 |
| | 737276 | −74 | | | | |
| | 679043 | −69 | | | | |
| | 674993 | −99 | | | | |
| | 693879 | −92 | | | | |
| | 701690 | −71 | | | | |
| | 731264 | −68 | −75 | 66 | | |
| SW620 | 648308 | −55 | | | | |
| | 674993 | −61 | | | | |
| | 674991 | −49 | 34 | 25 | | |
| | 701690 | −100 | 23 | 54 | | |
| | 737276 | −74 | | | | |
| | 674992 | −75 | | | | |
| HCC-2998 | 648308 | −99 | | | | |
| | 674992 | −96 | | | | |
| | 674993 | −96 | | | | |
| | 679043 | −88 | 22 | | | |
| | 693873 | −85 | | | | |
| | 693874 | −100 | 50 | | | |
| | 693875 | 10 | 53 | | | |
| | 693879 | −78 | | | | |
| | 698120 | −92 | | | | |
| | 701690 | −100 | | | | |
| | 720682 | −88 | | | | |
| | 737276 | −96 | | | | |
| | 737278 | −15 | 41 | 45 | 64 | |
| CNS Cancer | | | | | | |
| SF-268 | 665941 | 24 | 48 | | | |
| | 693874 | 10 | 49 | | | |
| | 693875 | −13 | 52 | | | |
| | 693879 | −56 | 59 | | | |
| | 701690 | −100 | 40 | 65 | | |
| SNB-19 | 679043 | −95 | | | | |
| | 674994 | 36 | 45 | 47 | 73 | 67 |
| | 693874 | −92 | | | | |
| | 693879 | −72 | | | | |
| | 701690 | −47 | 53 | | | |
| | 731265 | −87 | | | | |
| SF-295 | 665941 | 7 | 47 | | | |
| | 679043 | −88 | | | | |
| | 679047 | −53 | −50 | −54 | −44 | 70 |
| | 679046 | −52 | −58 | −65 | −56 | 51 |
| | 679993 | −76 | 34 | 46 | | |
| | 674991 | −31 | 31 | | | |
| | 693874 | −100 | 32 | | | |
| | 693875 | −69 | 47 | | | |
| | 693879 | −82 | 58 | | | |
| | 701690 | −100 | | | | |
| | 720683 | −70 | | | | |
| | 720682 | −78 | 53 | | | |
| SF-539 | 665940 | 63 | 99 | 43 | 62 | 47 |
| | 665941 | −48 | 47 | | | |
| | 671534 | −79 | | | | |
| | 693874 | −100 | 51 | | | |
| | 693875 | −92 | 51 | | | |
| | 698123 | 42 | 50 | | | |
| | 701690 | −100 | 44 | | | |
| | 720682 | −69 | 57 | | | |
| | 720683 | −67 | | | | |
| | 731264 | −73 | | | | |
| | 731262 | −80 | | | | |
| | 731265 | −79 | | | | |
| | 674992 | −62 | | | | |
| SNB-75 | 686562 | −28 | 28 | 64 | | |
| | 693874 | −96 | −21 | 6 | 27 | 6 |
| | 693875 | −42 | 44 | 81 | 94 | 60 |
| | 693879 | −62 | 55 | | | |
| | 701690 | −100 | 45 | | | |
| | 737276 | −87 | | | | |
| U251 | 731262 | −78 | | | | |
| | 674993 | −94 | | | | |
| | 679043 | −96 | | | | |

Section III

| Tumor type | NSC # | 10⁻⁴ | 10⁻⁵ | 10⁻⁶ | 10⁻⁷ | 10⁻⁸ |
|---|---|---|---|---|---|---|
| | | $10^{-4}$ | $10^{-5}$ | $10^{-6}$ | $10^{-7}$ | $10^{-8}$ |
| | | % Growth | | | | |
| | 693874 | −25 | 57 | | | |
| | 693879 | −100 | | | | |
| | 731263 | −85 | | | | |
| | 701690 | −100 | 42 | 53 | 46 | 62 |
| Melanoma | | | | | | |
| SK-MEL-2 | 648308 | −80 | | | | |
| | 693874 | −85 | | | | |
| | 693879 | −99 | | | | |
| | 701690 | −73 | 7 | −2 | −8 | −3 |
| | 731264 | 27 | 49 | | | |
| | 737276 | −62 | | | | |
| SK-MEL-28 | 674992 | −64 | | | | |
| | 671534 | −67 | 33 | 62 | 68 | 56 |
| | 679043 | −78 | | | | |
| | 693874 | −83 | | | | |
| | 701690 | −100 | 58 | | | |
| | 720683 | −85 | −55 | −31 | 31 | 74 |
| | 731262 | −81 | | | | |
| | 720682 | −85 | | | | |
| | 731265 | −69 | | | | |
| SK-MEL-5 | 648308 | −91 | | | | |
| | 671534 | −94 | | | | |
| | 674993 | −100 | 64 | | | |
| | 679043 | −91 | | | | |
| | 693874 | −100 | | | | |
| | 693875 | −83 | | | | |
| | 693879 | −100 | | | | |
| | 701690 | −100 | 58 | | | |
| | 720682 | −91 | | | | |
| | 720683 | −95 | | | | |
| | 731264 | −53 | 28 | | | |
| | 731265 | −67 | | | | |
| | 731278 | −78 | | | | |
| | 674992 | −100 | | | | |
| | 731262 | −84 | | | | |
| LOXIMVI | 674991 | −90 | 63 | | | |
| | 679043 | −84 | 45 | | | |
| | 648308 | −93 | | | | |
| | 693874 | −95 | 35 | | | |
| | 693875 | −95 | 52 | | | |
| | 701690 | −100 | 36 | | | |
| MALME-3M | 679043 | −88 | | | | |
| | 648308 | −80 | | | | |
| | 679534 | −88 | | | | |
| | 693874 | −78 | | | | |
| | 693879 | −100 | 44 | 62 | | |
| | 674993 | −86 | | | | |
| | 701690 | −100 | 38 | 43 | | |
| | 720682 | −89 | | | | |
| | 720683 | −87 | | | | |
| M14 | 679043 | −78 | | | | |
| | 693879 | −100 | | | | |
| | 701690 | −100 | | | | |
| | 720682 | −90 | | | | |
| | 731265 | −86 | | | | |
| UACC-257 | 731260 | −74 | | | | |
| | 671534 | −64 | | | | |
| | 674993 | −19 | 25 | | | |
| | 693874 | −100 | | | | |
| | 701690 | −83 | | | | |
| | 720682 | −64 | | | | |
| | 731265 | −87 | 40 | | | |
| | 731262 | −83 | | | | |
| | 737276 | −76 | | | | |
| UACC-62 | 731260 | −86 | | | | |
| | 648308 | −82 | | | | |
| | 665941 | 9 | 49 | | | |
| | 674991 | 5 | 57 | | | |
| | 674993 | −73 | 4 | | | |
| | 693874 | −92 | 48 | | | |
| | 693879 | −66 | | | | |
| | 720682 | −73 | 55 | | | |
| | 720683 | −85 | | | | |
| | 737276 | −91 | | | | |
| Ovarian Cancer | | | | | | |
| IGROVI | 674992 | −66 | | | | |
| | 671534 | −87 | | | | |
| | 674993 | −81 | | | | |
| | 693879 | −89 | 50 | 60 | 52 | |
| | 693880 | −21 | 37 | 60 | | |
| | 701690 | −100 | 40 | 60 | | |
| | 693874 | −100 | 52 | | | |
| | 737276 | −70 | | | | |
| OVCAR-3 | 674992 | −94 | | | | |
| | 671534 | −59 | | | | |
| | 674993 | −82 | | | | |
| | 679043 | −100 | | | | |
| | 693874 | −100 | | | | |
| | 693875 | −79 | | | | |
| | 693879 | −100 | | | | |
| | 701690 | −73 | | | | |
| | 737276 | −71 | | | | |
| OVCAR-4 | 698120 | −88 | | | | |
| | 674993 | −77 | | | | |
| | 679043 | −97 | | | | |
| | 693874 | −89 | | | | |
| | 693875 | −65 | 38 | | | |
| | 701690 | −100 | | | | |
| | 737276 | −73 | | | | |
| OVCAR-5 | 674992 | −96 | | | | |
| | 674993 | −82 | | | | |
| | 679043 | −98 | | | | |
| | 693874 | −98 | | | | |
| | 693879 | −100 | | | | |
| | 720682 | −87 | | | | |
| | 720683 | −71 | | | | |
| | 731264 | −49 | 51 | 39 | 46 | 52 |
| | 731265 | −83 | 43 | 34 | 40 | 63 |
| | 737276 | −89 | | | | |
| OVCAR-8 | 671534 | −78 | | | | |
| | 693874 | −71 | | | | |
| | 701690 | −100 | | | | |
| SK-OV-3 | 674992 | −63 | | | | |
| | 674993 | −36 | | −5 | | |
| | 693875 | −84 | | | | |
| | 693874 | −75 | | | | |
| | 737276 | −67 | | | | |
| Renal Cancer | | | | | | |
| 786-0 | 674992 | −89 | | | | |
| | 648308 | −95 | | | | |
| | 674993 | −66 | | | | |
| | 679043 | −97 | | | | |
| | 701690 | −100 | 36 | | | |
| | 720682 | −20 | 49 | | | |
| | 737276 | −74 | | | | |
| ACHN | 674993 | −68 | | | | |
| | 679043 | −90 | | | | |
| | 693874 | −100 | 50 | | | |
| | 693875 | −31 | 45 | | | |
| | 701690 | −77 | | | | |
| | 720682 | −21 | 55 | | | |
| | 731264 | −82 | | | | |
| | 731262 | −79 | | | | |
| | 737276 | −82 | | | | |
| CAKI-1 | 674992 | −94 | | | | |
| | 648308 | −71 | | | | |
| | 674993 | −92 | | | | |
| | 679043 | −100 | | | | |
| | 693879 | −87 | | | | |
| A498 | 671534 | −87 | | | | |
| | 648308 | −100 | | | | |
| RXF-393 | 674993 | −89 | | | | |
| | 671534 | −70 | 6 | | | |

-continued

Section III

| Tumor type | NSC # | Molar Concentration | | | | |
|---|---|---|---|---|---|---|
| | | $10^{-4}$ | $10^{-5}$ | $10^{-6}$ | $10^{-7}$ | $10^{-8}$ |
| | | % Growth | | | | |
| | 693875 | −62 | 42 | | | |
| | 701690 | −69 | | | | |
| | 701691 | 23 | 55 | 60 | 68 | 63 |
| TK-10 | 737276 | −73 | | | | |
| | 679043 | −93 | | | | |
| | 693874 | −100 | | | | |
| SN12C | 679043 | −85 | | | | |
| | 674993 | −93 | | | | |
| | 693874 | −100 | | | | |
| | 701690 | −100 | | | | |
| | 731264 | −67 | −99 | −4 | | |
| | 737276 | −64 | | | | |
| UO-31 | 674992 | −96 | | | | |
| | 648308 | −95 | | | | |
| | 679043 | −100 | | | | |
| | 693874 | −97 | | | | |
| | 674993 | −100 | | | | |
| | 701690 | −92 | | | | |
| | 737276 | −81 | | | | |
| Prostate Cancer | | | | | | |
| PC-3 | 737276 | −68 | | | | |
| | 674993 | −84 | | | | |
| | 693879 | −100 | | | | |
| | 679043 | −91 | 57 | | | |
| | 693874 | −80 | | | | |
| | 701690 | −38 | 52 | 59 | 28 | 28 |
| DV-145 | 679043 | −100 | | | | |
| | 693874 | −94 | | | | |
| | 693879 | −100 | | | | |
| | 720682 | −99 | | | | |
| | 720683 | −100 | | | | |
| | 731264 | −68 | −96 | 38 | | |
| | 731265 | −78 | | | | |
| | 674992 | −76 | | | | |
| | 731262 | −90 | | | | |
| | 737276 | −81 | | | | |
| Breast Cancer | | | | | | |
| MCF7 | 674992 | −65 | | | | |
| | 671533 | 56 | 65 | 48 | 101 | 50 |
| | 674993 | −71 | | | | |
| | 693874 | −83 | 56 | | | |
| | 693875 | −50 | 49 | | | |
| | 679043 | −78 | 45 | | | |
| | 701690 | −100 | | | | |
| MCF7/ADR-RES | 693879 | −54 | | | | |
| | 665941 | 1 | 63 | 69 | 68 | 56 |
| | 731265 | −53 | | | | |
| MDA-MB-435 | 679043 | −90 | 47 | | | |
| | 693874 | −92 | 54 | | | |
| | 671534 | −83 | | | | |
| | 701690 | −95 | | | | |
| | 720682 | −86 | | | | |
| | 731264 | −73 | | | | |
| | 731265 | −71 | −66 | | | |
| | 698124 | −74 | | | | |
| | 731260 | −79 | | | | |
| | 731262 | −73 | | | | |

-continued

Section III

| Tumor type | NSC # | Molar Concentration | | | | |
|---|---|---|---|---|---|---|
| | | $10^{-4}$ | $10^{-5}$ | $10^{-6}$ | $10^{-7}$ | $10^{-8}$ |
| | | % Growth | | | | |
| BT-549 | 674992 | −93 | | | | |
| | 665941 | 18 | 33 | | | |
| | 665943 | 12 | 28 | 52 | 42 | 44 |
| | 679043 | −82 | 57 | | | |
| | 674993 | −100 | | | | |
| | 693874 | −100 | | | | |
| | 701690 | −100 | | | | |
| | 720682 | −78 | | | | |
| | 731262 | −65 | | | | |
| H5-578T | 693879 | −49 | 55 | | | |
| MDA-MB-231 (ATCC) | 701690 | −41 | 39 | 56 | 58 | 45 |
| T-47D | 674993 | −49 | | | | |
| | 701690 | −54 | | | | |
| Renal Cancer | | | | | | |
| A498 | 643308 | −100 | | | | |
| | 671534 | −87 | | | | |
| Lymphoma | | | | | | |
| RL | 679043 | −45 | 33 | | | |
| | 679042 | −45 | 41 | | | |
| KD488 | 679048 | 54 | 51 | 34 | 100 | 52 |
| | 679043 | −45 | 30 | 62 | 54 | |
| | 679042 | −39 | 39 | | | |
| | 679047 | 29 | 45 | 56 | 71 | 78 |
| AS283 | 679043 | −34 | 37 | | | |
| | 679042 | −25 | 15 | 58 | 54 | |
| SU-DAL-7 | 679043 | −44 | 14 | | | |
| | 679042 | −42 | 29 | 57 | | |
| | 679047 | 42 | | | | |
| PA682 | 679043 | −33 | 45 | | | |
| | 679042 | −34 | 18 | | | |

Section IV. Summary of Anticancer Activity of Derivatives of Ethylene Methanedisulfonate Listed in Section II As shown in Sections II and III, the various derivative of ethylene methanedisulfonate (derivatives) were found to be active as anticancer agents against one or more of the 65 cancers. For example, some derivatives were found to prevent growth of the cells to 30% or less at $10^{-4}$ molar concentrations. Anticancer activities of some derivatives were found to be much higher than the others as the NCI screening show negative growth of human cancer cells when these derivatives were administrated. The percentage of cancers showing negative growth of tested human cancer cells for each derivative is summarized in tables 7-12 below. The derivatives in the tables are grouped using the same category as in the tables 1-6. The higher percentage may indicate that the anticancer activity levels of the derivatives are higher toward various cancers.

TABLE 7A

Summary of Anticancer Activity of Derivatives of Ethylene Methanedisulfonate with Improved Solubility Compared to Ethylene Methanedisulfonate $$\underset{R^2}{\overset{R^1}{>}}C\underset{SO_2-O-CH_2}{\overset{SO_2-O-CH_2}{<}}\vert \quad (I)$$

| NSC No. | R$^1$ | R$^2$ | Percentage of cancers showing negative growth cancers tested |
|---|---|---|---|
| 693879 | –CH$_2$–CH$_2$–O–SO$_3$Na | 1,2-disubstituted naphthalene: –CH$_2$– and –CH$_3$ | 10$^{-4}$ M conc. = 45/45 = 100%. Note: at 10$^{-4}$ M conc., 9 or 20% had –100% growth. |
| 674992 | 1-naphthylmethyl (–CH$_2$–naphthalene) | –CH$_2$–CH$_2$–O–Si(CH$_3$)$_2$– with –SO$_3$Na on CH$_2$ | 10$^{-4}$ M conc. = 45/48 = 93% |
| 693880 | H– | 2-acetylbenzenesulfonic acid group (phenyl with C(=O)CH$_3$ and SO$_3$H) | 10$^{-4}$ M conc. = 8/17 = 47% |
| 674991 | H– | –CH$_2$–CH$_2$–O–Si(CH$_3$)$_2$– with –SO$_3$Na on CH$_2$ | 10$^{-4}$ M conc. = 6/21 = 28.6% |
| 698122 | Na$^+$ | 8-quinolinyl–SO$_2$– | 10$^{-4}$ M conc. = 8/31 = 25.8% |
| 679044 | Na$^+$ | 1-naphthyl–SO$_2$– | 10$^{-4}$ M conc. = 1/4 = 25% |
| 671537 | H– | phthaloyl derivative: phenyl-C(=O)–NH–CH$_2$– and –C(=O)–OH | 10$^{-4}$ M conc. = 0/1 = 0 |
| 674994 | H– | –CH$_2$–CH$_2$–CH$_2$–O–SO$_3$Na | 10$^{-4}$ M conc. = 0/1 = 0 |
| NA | Br– | –CH$_2$–CH$_2$–SO$_2$– with –SO$_3$Na | No data |

TABLE 7B

Summary of Anticancer Activity of Derivatives of Ethylene Methanedisulfonate
with Improved Solubility Compared to Ethylene Methanedisulfonate

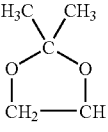
(II)

| NSC No. | R$^1$ | R$^2$ | Percentage of cancers showing negative growth cancers tested |
|---|---|---|---|
| 737275 | 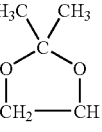 | 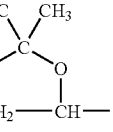 | 10$^{-4}$ M conc. = 1/5 = 20% |
| | | | 10$^{-4}$ M conc. = 0/1 = 0 |
| 698123 | 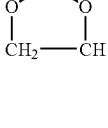 | —ONa | 10$^{-4}$ M conc. = 0/3 = 0 |
| 701691 | H— | —OCH$_3$ | 10$^{-4}$ M conc. = 0/6 = 0 |

TABLE 7C

Summary of Anticancer Activity of Derivatives of
Ethylene Methanedisulfonate with Improved
Solubility Compared to Ethylene Methanedisulfonate

| NSC No. | Compound structure | Percentage of cancers showing negative growth cancers tested |
|---|---|---|
| 686564 | 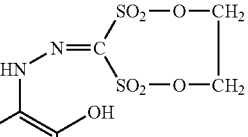 | 10$^{-4}$ M conc. = 0/5 = 0 |

TABLE 8A
Summary of Anticancer Activity of Derivatives of Ethylene Ethanedisulfonate
with Increased Lipophilicity Compared to Ethylene Methanedisulfonate
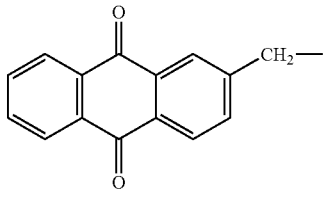
(I)
| NSC No. | R$^1$ | R$^2$ | Percentage of cancers showing negative growth cancers tested |
|---|---|---|---|
| 737276 | 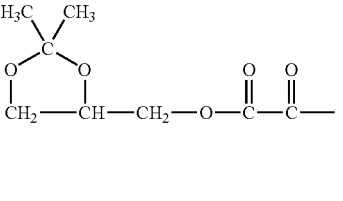 | 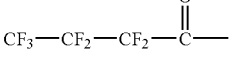 | 10$^{-4}$ M conc. = 49/55 = 89% |
| 720683 | 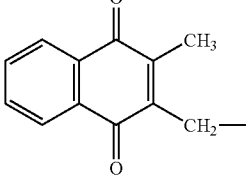 | 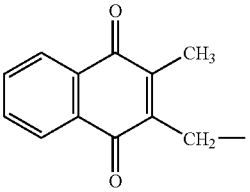 | 10$^{-4}$ M conc. = 24/35 = 69% |
| 737277 | 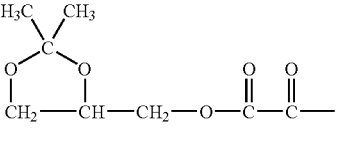 | 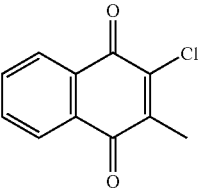 | 10$^{-4}$ M conc. = 6/9 = 67% |
| 737278 | 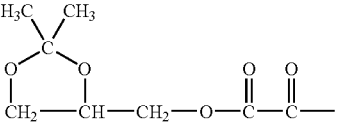 | 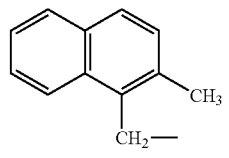 | 10$^{-4}$ M conc. = 8/12 = 67% |
| 693873 | 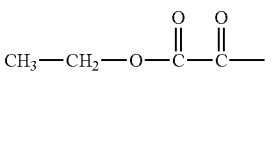 | CH$_3$—CH$_2$—O—C(=O)—C(=O)— | 10$^{-4}$ M conc. = 16/44 = 36% |

TABLE 8B

Summary of Anticancer Activity of Derivatives of Ethylene Methanedisulfonate with Increased Lipophilicity Compared to Ethylene Methanedisulfonate $$\begin{array}{c} R^1 \\ \phantom{R^1}C=C \\ R^2 \end{array} \begin{array}{c} SO_2-O-CH_2 \\ \phantom{xxx}| \\ SO_2-O-CH_2 \end{array} \quad (I)$$

| NSC No. | R¹ | R² | Percentage of cancers showing negative growth cancers tested |
|---|---|---|---|
| 737275 | (2,2-dimethyl-1,3-dioxolan-4-yl)methyl-O-C(O)- | (2,2-dimethyl-1,3-dioxolan-4-yl)methyl-O-C(O)-C(O)-O- | $10^{-4}$ M conc. = 1/5 = 20% |
| 698123 | (2,2-dimethyl-1,3-dioxolan-4-yl)methyl-O-C(O)- | —ONa | $10^{-4}$ M conc. = 0/3 = 0 |

TABLE 9

Summary of Anticancer Activity of Derivatives of Ethylene Methanedisulfonate with Potential for Halogenation $$\begin{array}{c} R^1 \\ \phantom{R^1}C \\ R^2 \end{array} \begin{array}{c} SO_2-O-CH_2 \\ \phantom{xxx}| \\ SO_2-O-CH_2 \end{array} \quad (I)$$

| NSC No. | R¹ | R² | Percentage of cancers showing negative growth cancers tested |
|---|---|---|---|
| 648308 | I— | I— | $10^{-4}$ M conc. = 48/48 = 100% |
| 679046 | I— | 2-naphthoyl- | $10^{-4}$ M conc. = 1/1 = 100%<br>$10^{-5}$ M conc. = 1/1 = 100%<br>$10^{-6}$ M conc. = 1/1 = 100%<br>$10^{-7}$ M conc. = 1/1 = 100%<br>$10^{-8}$ M conc. = 0/1 = 0 |
| 648304 | Br— | Br— | $10^{-4}$ M conc. = 1/3 = 33% |
| 648305 | H— | Br— | $10^{-4}$ M conc. = 1/3 = 33% |
| 648307 | Cl— | Cl— | $10^{-4}$ M conc. = 0/5 = 0 |
| 648309 | H— | I— | $10^{-4}$ M conc. = 0/2 = 0 |
| 665942 | H— | F— | $10^{-4}$ M conc. = 0/1 = 0 |
| 665943 | H— | Br— | $10^{-4}$ M conc. = 0/1 = 0 |
| 671533 | F— | benzyl (—CH₂—C₆H₅) | $10^{-4}$ M conc. = 0/1 = 0 |
| NA | Br— | 1-naphthoyl- | No data |
| NA | Br— | —CH₂—CH₂—SO₂— with SO₃Na branch | No data |

TABLE 10

Summary of Anticancer Activity of Derivatives of Ethylene Methanedisulfonate with the Combination of the Quinone Moiety Characteristic with Alkylating Moiety Characteristic $$\begin{matrix} R^1 & SO_2-O-CH_2 \\ & \diagdown C \diagup & | \\ R^2 & SO_2-O-CH_2 \end{matrix} \quad (I)$$

| NSC number | $R^1$ | $R^2$ | Percentage of cancers showing negative growth from available data |
|---|---|---|---|
| 701690 | $CH_3-\overset{O}{\underset{\|}{C}}-$ | 2-methyl-3-(CH$_2$—)-1,4-naphthoquinone | $10^{-4}$ M conc. = 53/53 = 100% <br> $10^{-5}$ M conc. = 1/21 = 5% <br> $10^{-6}$ M conc. = 1/7 = 14% |
| 693874 | H— | 2-methyl-3-(CH$_2$—)-1,4-naphthoquinone | $10^{-4}$ M conc. = 46/47 = 98% <br> $10^{-5}$ M conc. = 2/17 = 12% |
| 737276 | 9,10-anthraquinone-2-CH$_2$— | $(CH_3)_2C(OCH_2CH(-)CH_2)(O)-CH_2-O-C(O)-C(O)-$ | $10^{-4}$ M conc. = 49/55 = 89% |
| 720682 | $CF_3SO_2-$ | 2-methyl-3-(CH$_2$—)-1,4-naphthoquinone | $10^{-4}$ M conc. = 38/47 = 81% <br> $10^{-5}$ M conc. = 1/6 = 17% |
| 731262 | $Cl-CH_2-\overset{O}{\underset{\|}{C}}-$ | 2-methyl-3-(CH$_2$—)-1,4-naphthoquinone | $10^{-4}$ M conc. = 28/35 = 80% |
| 720683 | $CF_3-CF_2-CF_2-\overset{O}{\underset{\|}{C}}-$ | 2-methyl-3-(CH$_2$—)-1,4-naphthoquinone | $10^{-4}$ M conc. = 24/35 = 69% <br> $10^{-5}$ M conc. = 2/2 = 100% <br> $10^{-6}$ M conc. = 2/2 = 100% |

TABLE 10-continued

Summary of Anticancer Activity of Derivatives of Ethylene Methanedisulfonate with the
Combination of the Quinone Moiety Characteristic with Alkylating Moiety Characteristic $$\begin{array}{c} R^1 \diagdown \phantom{C} \diagup SO_2-O-CH_2 \\ C \\ R^2 \diagup \phantom{C} \diagdown SO_2-O-CH_2 \end{array}$$ (I)

| NSC number | $R^1$ | $R^2$ | Percentage of cancers showing negative growth from available data |
|---|---|---|---|
| 731265 | CH₃—CH=CH—C(=O)— | 2-methyl-3-(CH₂—)-1,4-naphthoquinone | $10^{-4}$ M conc. = 34/43 = 79%<br>$10^{-5}$ M conc. = 1/5 = 20% |
| 737277 | 2-methyl-3-(CH₂—)-1,4-naphthoquinone | (CH₃)₂C(O—CH₂—CH(—)—CH₂—O—C(=O)—C(=O)—)(O—) acetonide | $10^{-4}$ M conc. = 6/9 = 67% |
| 737278 | 2-chloro-3-methyl-1,4-naphthoquinone (CH₂— via methyl) | (CH₃)₂C(O—CH₂—CH(—)—CH₂—O—C(=O)—C(=O)—)(O—) acetonide | $10^{-4}$ M conc. = 8/12 = 67% |
| 731264 | CH₃—CH=CH—C(=O)— | 2-chloro-3-methyl-1,4-naphthoquinone (CH₂— via methyl) | $10^{-4}$ M conc. = 22/34 = 65%<br>$10^{-5}$ M conc. = 3/6 = 50%<br>$10^{-6}$ M conc. = 1/6 = 25% |
| 693875 | H— | 2-(CH₂—)-anthraquinone | $10^{-4}$ M conc. = 23/37 = 62% |
| 731263 | CH₃—CH=CH—C(=O)— | 2-(CH₂—)-anthraquinone | $10^{-4}$ M conc. = 18/36 = 50% |

TABLE 10-continued

Summary of Anticancer Activity of Derivatives of Ethylene Methanedisulfonate with the Combination of the Quinone Moiety Characteristic with Alkylating Moiety Characteristic $$\begin{array}{c} R^1 \diagdown \phantom{C} \diagup SO_2-O-CH_2 \\ \phantom{R^1}C \\ R^2 \diagup \phantom{C} \diagdown SO_2-O-CH_2 \end{array} \quad (I)$$

| NSC number | $R^1$ | $R^2$ | Percentage of cancers showing negative growth from available data |
|---|---|---|---|
| 731260 | H— | 3-chloro-2-methyl-1,4-naphthoquinone | $10^{-4}$ M conc. = 16/37 = 43% |
| 698124 | $CH_3CH_2$—O—$CH_2$— | 2-methyl-3-(CH$_2$—)-1,4-naphthoquinone | $10^{-4}$ M conc. = 8/25 = 32% |

TABLE 11

Summary of Anticancer Activity of Derivatives of Ethylene Methanedisulfonate That Are Cancer Cell Stimulators and Cancer Cell Inhibitors $$\begin{array}{c} R^1 \diagdown \phantom{C} \diagup SO_2-O-CH_2 \\ \phantom{R^1}C \\ R^2 \diagup \phantom{C} \diagdown SO_2-O-CH_2 \end{array} \quad (I)$$

| NSC No. | $R^1$ | $R^2$ | Percentage of cancers showing negative growth cancers tested |
|---|---|---|---|
| 720685 | H— | 3,5,6-trichloro-2-methylpyrazine | $10^{-4}$ M conc. = 1/4 = 25% |
| 372239 | H— | $CH_3$— | $10^{-4}$ M conc. = 2/12 = 17% |
| 720685 | H— | 3,5,6-trichloro-2-methylpyrazine | $10^{-4}$ M conc. = 1/4 = 25% |
| 372239 | H— | $CH_3$— | $10^{-4}$ M conc. = 2/12 = 17% |
| 671536 | H— | phthalimidomethyl | $10^{-4}$ M conc. = 0/2 = 0 |
| 671537 | H— | 2-(carboxamidomethyl)benzoic acid | $10^{-4}$ M conc. = 0/1 = 0 |
| 665942 | H— | F— | $10^{-4}$ M conc. = 0/1 = 0 |
| 671535 | H— | $CH_3(CH_2)_6CH_2$—O—$CH_2$— | $10^{-4}$ M conc. = 0/1 = 0 |

TABLE 12A

Summary of Anticancer Activity of Derivatives of Ethylene Methanedisulfonate That Are Not Grouped in a Common Characteristic.

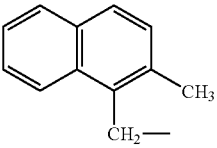
(I)

| NSC No. | R$^1$ | R$^2$ | Percentage of cancers showing negative growth cancers tested |
|---|---|---|---|
| 679043 | H— | 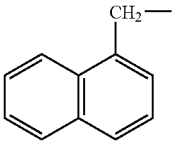 | $10^{-4}$ M conc. = 48/48 = 100%<br>$10^{-5}$ M conc. = 2/22 = 9%<br>Note that at $10^{-4}$ M conc., 4 or 8% had −100% growth |
| 674993 | CH$_3$—C(=O)— | 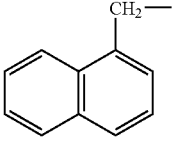 | $10^{-4}$ M conc. = 43/45 = 96%<br>$10^{-5}$ M conc. = 1/4 = 25% |
| 671534 | H— | 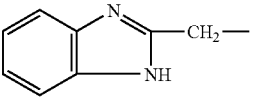 | $10^{-4}$ M conc. = 42/50 = 84% |
| 698120 | CH$_3$CH$_2$—O—CH$_2$— | CH$_3$CH$_2$—O—CH$_2$— | $10^{-4}$ M conc. = 22/42 = 52% |
| 679042 | H— | 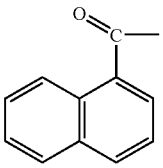 | $10^{-4}$ M conc. = 12/32 = 38% |
| 679047 | H— | 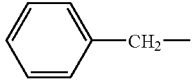 | $10^{-4}$ M conc. = 1/3 = 33% |
| 634863 | H— | 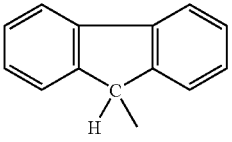 | $10^{-4}$ M conc. = 7/24 = 29% |
| 686562 | H— | 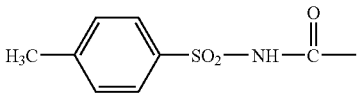 | $10^{-4}$ M conc. = 11/38 = 29% |
| 665941 | —CH$_2$CH$_2$CN | —CH$_2$CH$_2$CN | $10^{-4}$ M conc. = 3/32 = 9% |
| 648303 | H— | H$_3$C—C$_6$H$_4$—SO$_2$—NH—C(=O)— | $10^{-4}$ M conc. = 0/3 = 0 |
| NA | H— | 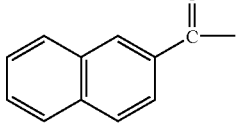 | No data |

TABLE 12B

Summary of Anticancer Activity of Derivatives of ethylene methane-disulfonate That Are Not Grouped in a Common Characteristic.

$$R^1\!\!\diagdown\!\!\!\!\!\!\!\!\diagup\!\!SO_2\!\!-\!\!O\!\!-\!\!CH_2 \atop R^2\!\!\diagup C\!\!=\!\!C\!\!\diagdown\!\!SO_2\!\!-\!\!O\!\!-\!\!CH_2 \qquad (II)$$

| NSC No. | $R^1$ | $R^2$ | Percentage of cancers showing negative growth cancers tested |
|---|---|---|---|
| 698121 | CH$_3$— | $CH_3\!-\!\underset{\underset{O}{\|\|}}{C}\!-$ | $10^{-4}$ M conc. = 1/8 = 0 |

As shown in the data above, some derivatives with a specific functional group may be effective to inhibit the growth of human cancer cells. For example, for all the derivatives with quinone moiety characteristics, negative growth of cancer cells were found among various cancers. The percentage of cancers showing negative growth ranges from 32-100%. The anticancer activities of the derivatives with a functional group of

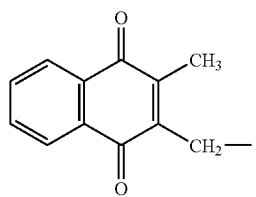

were shown to be highest. The derivatives with a functional group of

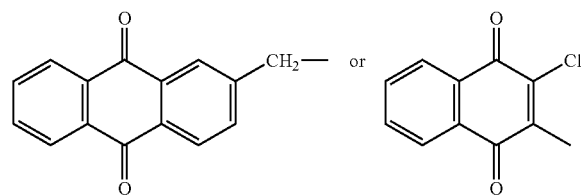

also showed higher anticancer activates.

As shown in Table 7A and Table 12A, two derivatives, NSC No. 693879 and 679043 having a functional group of

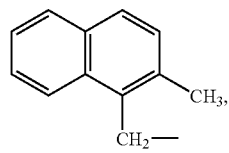

show the highest anticancer activity as negative growth of human cancer cells were found to be 100% for 45 and 48 cancers screened, respectively.

Also as shown in Table 7A and Table 12A, three derivatives having a functional group of

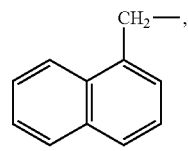

NSC No. 674992, 674993 and 671534, show higher anticancer activity. The negative growth of human cancer cells ranges from 84% to 96% for over forty five (45) cancers screened. The higher anticancer activity and potency of these three derivatives may be due to their molecular structures. For example, the flat polycyclic aromatic molecular ligands by intercalating between the heterocyclic Watson crick base pairs may confer to the attached cyclic binary alkylating ethylene methanedisulfonate ester more or less transient, durably favorable conformation, or propinquity to normal somatic or cancerous genetic material or cellular substrates, thus providing selective chemistry to these agents.

Table 3 shows that a derivative with $R^1$ and $R^2$ of iodide (NSC No. 648308) has the highest anticancer activities among this category. For 48 cancers screened, negative growth of human cancer cells is 100%.

Section V. Syntheses of Derivatives of Ethylene Methanedisulfonate

The compounds of the present application are all derivatives of the following ester:

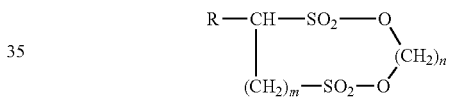

where R=H, n=2, and m=0, i.e., ethylene methanedisulfonate

The present disclosure discloses a method to replace the active hydrogens of ethylene methanedisulfonate. In some embodiments, an active hydrogen of ethylene methanedisulfonate may be removed by using NaH to replace the active hydrogen with Na or other radicals in an reaction. For example, NaH may be used to replace the active hydrogens of Ethylene Methanedisulfonate as shown in the reaction below. As shown, the use of NAH avoids the ring opening side reaction described above.

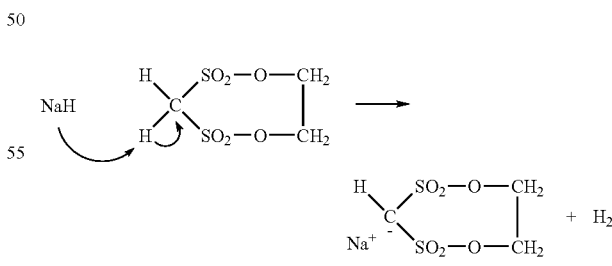

In some examples, excess amounts of NaH may be used in the above reaction.

The use of NaH has various advantages. For example, the standard procedure for the replacement of active hydrogens in such structures as diethyl malonate, CH$_2$(COOEt)$_2$ involves the use of bases, such as NaOCH$_3$:

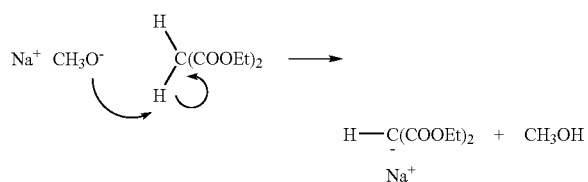

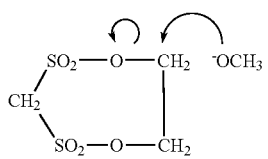

When the above procedure is used to replace the active hydrogen of ethylene methanedisulfonate, ethylene methanedisulfonate may be susceptible to nucleophilic attack by $^-OCH_3$ as shown below:

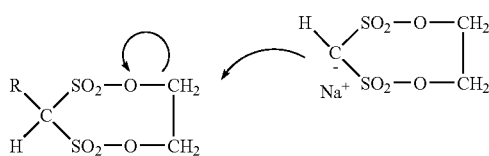

Thus, the ring of ethylene methanedisulfonate may be opened. However, when NaH is used, hydrogen gas is formed as shown by the reaction above. Thus, the ring opening may be avoided because of lack of sufficient nucleophiles in the reaction steps.

Further, the use of excess amounts of NaH during hydrogen replacement may minimize the self-destruction of the ester and its derivatives by the corresponding anions as shown below:

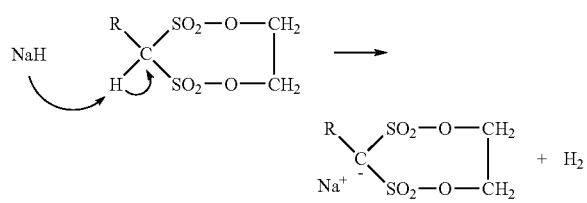

The use of excess NaH may immediately convert the product of the alkylation reaction into its sodium salt as shown in the reaction below:

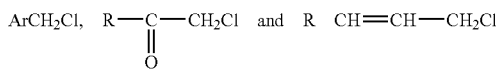

Because the sodium salts have negatively-charged carbon, they are much less susceptible to nucleophilic ring openings than the unionized form.

Further, the present application discloses that synthesis of a large number of potential anticancer therapeutic agents, such as derivatives of ethylene methanedisulfonate, by the reaction of one or more electrophilic reagents with the alkali salts of ethylene methanedisulfonate. The electrophilic reagents include, but are not limited to: aliphatic and aromatic carboxylic acid halides and sulfonyl halides, aromatic and imidohalides, activated halides, such as $ArCH_2Cl$, $R-\underset{\underset{O}{\|}}{C}-CH_2Cl$ and $R-CH=CH-CH_2Cl$ As discussed above, the reaction of elecrophilic reagents with the alkali salts of ethylene methanedisulfomate enables the synthesis of a very large number of potential anticancer therapeutic compounds.

In addition to the preparation of both mono and disubstitution products with these reagents, an additional type is made available via the enol form of the monosubstituted keto esters:

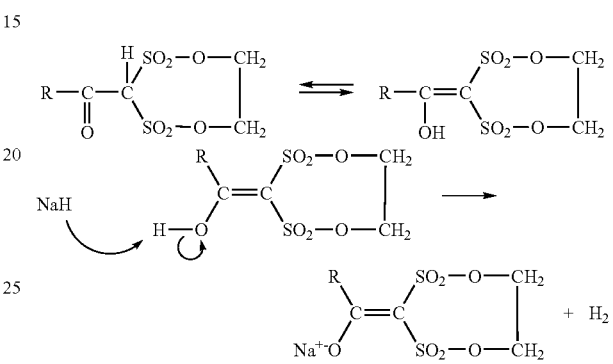

The examples of synthesis are disclosed below.

EXAMPLE 1

An Improved Method for the Preparation of Ethylene Methanedisulfonate

The required methanedisulfonylchloride was prepared by a modification of the method described by M. Fild and H. P. Riecke, Chem. Zeitung, 109(9); 391, (1976). To 275 mL (3 moles) of phosphorus oxychloride cooled in ice to 5°-10° C. in an ice bath in a one liter, 3-necked flask, equipped with a mechanical stirrer, dropping funnel, thermometer, and reflux condenser with exit above, but not into, a water trap, was added 198 mL (3 moles) of chlorosulfonic acid over 30 min.

Subsequently, 103 mL (1.5 M+20% excess) of acetic acid was added over a period of 15-20 min.

The ice bath was replaced with a heating mantle and the mixture was heated over 30 min to reflux at a temperature of 90-95° C.

The temperature of the mixture was gradually raised from 90-95° C. to 120-135° C. over a period of 1.5 hrs. with copious HCl evolution.

The mixture was then stirred and heated at 140-145° C. for about 4 hrs. Polyphosphoric acid separated during this time. The mixture was decanted from the polyphosphoric acid and, after a 15 mL $POCl_3$ rinse, was distilled with a water aspirator vacuum of about 15 mm. After removal of the $POCl_3$, the final residue was distilled at 0.5 mm and 104° C. to give 255 g (79.8% based on $ClSO_3H$ used) of $CH_2(SO_2Cl)_2$.

EXAMPLE 2

Synthesis of Ethylene Methanedisulfonate

To 650 mL of tetrahydrofuran, cooled to −25° C. in a Dowanol-Dry Ice bath, was added 42.6 g (0.2 mole) of $CH_2(SO_2Cl)_2$ and 13.64 g (0.2 mole) of ethylene glycol, rinsed in with 50 mL of CH$_3$CN. Then 42.6 g (0.421 moles) of KOH dried triethylamine in 100 mL of tetrahydrofuran was added dropwise to the stirred solution over about 30 min., followed by a further hour of stirring with the temperature rising slowly from −25° C. to −2° C.

After standing overnight, the solution was filtered and the solid was rinsed with 100 mL of tetrahydrofuran to give 58.3 g of N(Et)$_3$$^+$HCl$^−$. The 55 g theory for the salt had been augmented by a couple of grams of a sticky orange gum after standing overnight.

After removal of the tetrahydrofuran in a 15 mm vacuum distillation, the residue was taken up in 150 mL of water, filtered, air dried, then triturated with 100 mL of ethanol to give 22.3 g of crude solid. The solid was purified by extraction in a Soxhlet with 200 mL of CH$_2$Cl$_2$ as the solvent to give 17.9 g of a crystalline solid.

A second preparation (0.3 mole) was carried out to give a combined yield of 53.8 g of crude product with 46.8 g (46.3%) yield from the first Soxhlet extractions which then gave 41.8 g (41.3%) overall yield of highly purified ethylene methanedisulfonate, m.p. 176-180° C. (348948).

EXAMPLE 3

Preparation of Reagents Used in the Synthesis of the Ethylene Methanedisulfonate Derivatives 2-chloromethyl-3-methyl-1,4-napthoquinone A mixture of 17.2 g (0.1 mole) of 2-methyl-1,4-napthoquinone and 6 g (0.2 mole) of paraformaldehyde was heated to 60° C. in 50 mL of glacial acetic acid and stirred while dry HCl was bubbled through the solution for about 3 hrs. To the cooled mixture was added 200 mL of water, the solid was filtered and rinsed with 50 mL of water. It was then suspended in 200 mL of CH$_2$Cl$_2$, filtered, rinsed with CH$_2$Cl$_2$, and the filtrate was water washed, dried, and evaporated to leave 20.5 g of crude 2-methyl-3-chloromethyl-1,4-napthoquinone. The crude product was purified by sublimation at about 100° C. and pressure of 0.05 mm to give 12.7 g. Since there had been some splatter during the sublimation, the product was resublimed to give 12.1 g (55% yield), m.p. 102-104° C.

EXAMPLE 4

Preparation of 2,2-dimethyl-1,3-dioxa-2-sila-4-thia-cyclohexane-4,4-dioxide,

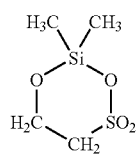

To 25 mL of dichlorodimethylsilane in a 100 mL r.b. flask was added 10 g of isethionic acid sodium salt and the mixture was heated to reflux with stirring for 20 hrs. The excess dichlorodimethylsilane was distilled and the residue transferred to a short-path distillation tube with a CH$_2$Cl$_2$ rinse. The residue was distilled at 145-175° C., 0.2 mm pressure, to give 8.25 g (67%) of a viscous liquid.

EXAMPLE 5

Preparation of

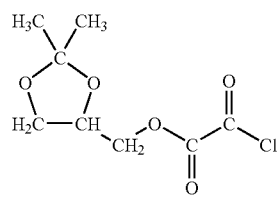

To 15 g of Solketal in 25 mL of CH$_2$Cl$_2$ was added, dropwise, 14 g of oxalyl chloride in 25 mL of CH$_2$Cl$_2$. After overnight stirring the CH$_2$Cl$_2$ was removed to leave 24 g of solketalyl oxalyl chloride (solkalyloxalyl chloride).

EXAMPLE 6

Preparation of

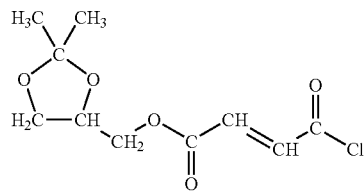

To a suspension of 2.5 g of NaH in 100 mL of glyme was added 12 g of Solketal in portions. After the addition the mixture was stirred overnight, filtered, and the filtrate was added dropwise rapidly to 13.8 g of fumaryl chloride in 100 mL of glyme followed by chunks of the sodium salt which had been removed by filtration. The mixture was stirred overnight and then filtered. After the glyme was removed by distillation the residue was taken up in 250 mL of cyclohexane. After 3 days the cyclohexane was decanted from the orange gum and solid. This residue, 14 g (62%) of solketalyl fumaryl chloride, was taken up in 200 mL of glyme and the solution was used as the reagent for the subsequent reactions with ethylene methanedisulfonate and its derivatives.

EXAMPLE 7

Preparation of Ethylene Methanedisulfonate Derivatives,

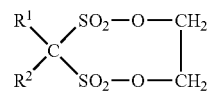

EXAMPLE 8

Halogenation a) $Br_2$ Double Substitution.

A solution of 2.02 g (0.01 mole) of ethylene methanedisulfonate in 30 mL of 0.4 molar NaOH was added slowly to 4 g (0.025 mole) of $Br_2$ stirred in 100 mL of ice cooled $H_2O$. After 5 min, 3.44 g of solid was recovered, suspended in 20 mL of 0.5 molar NaOH, filtered, washed, and dried to give 3.33 g (92%) of ethylene dibromomethanedisulfonate, m.p. 214-220° C. (91-4).

b) $Br_2$ Monosubstitution

A solution of 2.02 g of ethylene methanedisulfonate in 25 mL of 0.5 molar NaOH was added to a solution of 1.8 g of $Br_2$ in 100 mL of ice cooled $H_2O$. The solution was filtered to give 2.46 g of solid which was stirred vigorously in 25 mL of 0.5 molar NaOH, filtered, rinsed and the filtrate acidified with 7 mL of 2 molar HCl to give 1.53 g (54.5%) of ethylene bromomethanedisulfonate, m.p. 128-134° C. (91-5).

c) $Cl_2$ Mono and Disubstituted

A solution of 1.25 g of $KMnO_4$ and 7.8 mL of conc. HCl in 115 mL of ice cooled $H_2O$ was stirred for 2 hrs. To this solution was added 2.02 g of ethylene methanedisulfonate in 25 mL of 0.5 molar NaOH. The solid obtained after acidification was placed in 15 mL of 0.5 M NaOH and the filtrate acidified to give 1.1 g of ethylene chloromethanedisulfonate, m.p. 85-88° C. (91-6).

A sample of the base insoluble precipitate was crystallized from $CH_2Cl_2$-cyclohexane to give a solid, m.p. 183-193° C. (91-7).

d) $I_2$ Monostitution

A solution of 2.02 g of ethylene methanedisulfonate in 25 mL of 0.5 M NaOH was added to an ice cooled solution of 3.2 g of I and 3.5 g of KI in 75 mL of $H_2$.

Acidification gave 2.32 g (71%) of ethylene iodomethanedisulfonate, m.p. 144-160° C. (91-9).

e) F Monosubstitution

The fluorinating agent used was N-fluorobenzenesulfonimide obtained from PCR Chemicals (Gainesville Fla.). To a suspension of 0.34 g of NaH in 50 mL of tetrahydrofuran was added 2.45 g of ethylene methanedisulfonate followed by 3.8 g of N-fluorobenzenesulfonimide in 25 mL of acetonitrile. After about 15 min, 25 mL of $CH_2Cl_2$ was added, the solution was filtered, and the product was isolated by crystallization from $CH_2Cl_2$-cyclohexane to give 0.49 g of ethylene fluoromethanedisulfonate, m.p. 84-86° C. (93-2).

EXAMPLE 9

Ketone Derivatives

The ketone derivatives of ethylene methanedisulfonate were all prepared by the same general method, the addition of R(C=O)Cl or $RSO_2Cl$ to the sodium salt of ethylene methanedisulfonate which had been prepared using NaH in a glyme solution.

EXAMPLE 10

2-naphthoyl Chloride and 1-naphthoyl Chloride

To a suspension of 3 g NaH in 50 mL of glyme was added 1.0 g of ethylene methanedisulfonate. To this solution was added 1.1 g of 2-naphthoyl chloride and the $H_2$ evolved was measured. The theoretical amount of $H_2$ evolved in about 45 min. The solvent was then removed from the solution on a rotary evaporator. The residue was taken up in 50 mL of water and washed with $CH_2Cl_2$. The water solution was acidified and an oil separated which was then extracted with $CH_2Cl_2$ which was dried over $MgSO_4$, and evaporated to leave 1.65 g (93%) of crude product. Subsequent crystallization from $CH_2Cl_2$-cyclohexane gave 1.49 g (84%) ethylene 2-naphthoylmethanedisulfonate, m.p. 150-158° C. (95-4).

Similarly, 8-quinolinesulfonylchloride was used to give the sodium salt of ethylene 8-quinolylmethanedisulfonate (97-4) which was isolated by filtration of the glyme reaction solution followed by a $CH_2Cl_2$ rinse which left NaCl with the product.

EXAMPLE 11

1-naphthoylchloride

To a suspension of 0.336 g (0.014 moles) of NaH in 50 mL of glyme, was added 1.13 g of ethylene methanedisulfonate. After stirring about ten minutes, 1.068 g of 1-naphthoylchloride and the $H_2$ collected. After 3.5 hrs. of stirring, the theoretical amount of $H_2$, 135 mL, was collected.

The solution was filtered through filteraid which was washed with $CH_2Cl_2$ and the filtrate removed by distillation at 20 mm and the residue was taken up in 25 mL of water which was washed with 25 mL of $CH_2Cl_2$, and acidified with 10 mL of 2 M HCl to give 1.6 g of solid, m.p. 130-140° C. The solid was redissolved in 10 mL of 5% $NaHCO_3$, filtered through filteraid, and acidified to give 1.28 g (64%) of ethylene 1-naphthoylmethanedisulfonate, m.p. 152-156° C. (95-6).

EXAMPLE 12

Azo Derivative

To a solution of 0.433 g of ethylene methanedisulfonate in 6 mL of 1 M NaOH was added 0.6 g of 1-diazo-2-naphthoyl-4-sulfonic acid. After 2 days the solution was cooled on ice and 1 mL of $CH_3SO_3H$ was added. After about 30 min the solid which had separated was dried by pressing on filter paper to give 0.3 g (31%) of solid, m.p. 165-180° C. (96-3).

EXAMPLE 13

Synthesis of the Type $Ar-CH_2Cl$, $ROCH_2Cl$, and Other Halogens Subject to Nucleophilic Replacement with Sodium Ethylene Methanedisulfonate To 0.6 g of NaH in 75 mL of glyme was added 2.02 g (0.01 mole) of ethylene methanedisulfonate followed after 15 min by 2.53 g (0.01 mole) of 2-chloromethylanthraquinone. No $H_2$ was generated after about 15 min so 0.3 g (0.002 mole) of KI was added. The mixture was stirred, the $H_2$ was collected overnight (270 mL total vs. 240 mL theory), and then filtered through filteraid. The glyme was removed through a rotary evaporator at 20 mm and the residue taken up in 100 mL of 1 M HCl, filtered, and dried to give 4.01 g (95%) 2-anthroquinoyl-1,1-ethanedisulfonate, m.p. darken at 205° C., dec. 245° C. (96-10).

To a suspension of 1.0 g of NaH in 75 mL of glyme was added 2.02 g of ethylene methanedisulfonate. After 15 min 2.21 g of 2-chloromethyl-3-methyl-1,4-naphthoquinone was added and the $H_2$ collected with vigorous stirring to give 230 mL (240 mL theory) in 35 min. The solution was filtered and the solid rinsed with glyme. Glyme was removed from the filtrate and the residue was taken up in 100 mL of 1 M HCl to give 2.9 g (75%) ethylene (3-methyl-1,4-naphtho-2-quinoyl)-1,1-ethanedisulfonate, m.p. dark 210° C., 235-240° C. dec. (96-9).

Similarly, to a solution of 0.36 g of 95-4 in 30 mL of 5% NaHCO$_3$ was added 10 mL of 0.1 M KI$_3$. After stirring overnight a total of 0.234 g (48.5%) of 95-5 was obtained.

To a solution of 0.3564 g of 95-6 in 10 mL of 5% NaHCO$_3$ was added 10 mL of 0.1 M Br$_2$ in water. After an immediate precipitate, the solid was filtered after about 15 min. to give 0.3525 g (81%) of 95-7, m.p. 178-184° C.

To a filtered solution of 0.4 g NaH in 50 mL of glyme was added 1.6828 g of 2-(chloromethyl)benzimidazole. The mixture was stirred overnight and filtered to give 1.1 g of ethylene 2-benzimidazolyl-1,1-ethanedisulfonate which was purified by trituration in CH$_2$Cl$_2$ to give 0.895 g (27%), m.p. 222-233° C. of 95-1.

To a solution of 0.34 g of NaH in glyme and 1.1534 g of ethylene methanedisulfonate was added 1.09 g of 1-chloromethyl-2-methylnaphthalene and 0.85 g NaI. After 2 hrs. stirring the solvent was removed and the residue taken up in a mix of 10 mL of 1 M HCl and 25 mL of CH$_2$Cl$_2$. The CH$_2$Cl$_2$ was washed with 10 mL of 1 M NaHSO$_3$, dried, and concentrated to give 1.49 g (73%) of ethylene 2-methyl-1-naphyl-1, 1-ethanedisulfonate, m.p. 191-196° C. (95-2).

After the preparation of the sodium salt of ethylene methanedisulfonate with NaH in glyme (0.6 g of NaH and 5 g of the ester), 5 g of 4-methylbenzenesulfonylisocyanate was added. After an immediate reaction the ethylene(4-methylbenzenesulfonamidocarbonyl)methanedisulfonate, 1.73 g, m.p. 172-178° C., was obtained by sodium bicarbonate extraction and acidification (91-3).

To a solution of 2.02 g of ethylene methanedisulfonate in 25 mL of 0.5 M NaOH was added a solution of 3.2 g of I$_2$ and 3.5 g of KI in 75 mL of water. The solid which separated (2.3 g) was triturated with 20 mL of 0.5 M NaOH and the insoluble solid was purified in CH$_2$Cl$_2$ to give 0.98 g, m.p. 208-222° C., of ethylene diiodomethanedisulfonate (91-8).

To a solution of 3 g of ethylene methanedisulfonate in 50 mL of THF with 0.3 g of NaH was added 1.0 g of CH$_2$=CH—CN. After the addition of 10 mL of t-butyl alcohol the disubstituted ester was isolated by treatment with 0.5 M NaOH and 0.53 g (m.p. 138-141° C.) was obtained (93-1).

To a solution of 2.4 g of ethylene methanedisulfonate in 20 mL of THF and 0.35 g of NaH was added 3.8 g of N-fluorobenzene sulfonimide in 25 mL of CH$_3$CN. The product was isolated by crystallization from CH$_2$Cl$_2$ and cyclohexane to give 0.4 g of ethylene fluoromethane disulfonate which was brominated in H$_2$O to give ethylene fluorobromomethanedisulfonate, m.p. 82-90° C. (93-3).

To a solution of 2.6 g of ethylene methanedisulfonate in 50 mL of glyme and 1.0 g of NaH was added 3 g of benzyl chloride. After rotoevaporation of the glyme the residue was taken up in 25 mL of 0.5 M NaOH, filtered, and acidified to give 1.21 g of ethylene benzyl methanedisulfonate, m.p. 170-174° C. (90-3).

This compound (90-3) was dissolved in 50 mL of glyme and 0.13 g of NaH with the addition of 1.4 g of fluorobenzene sulfonimide to give 0.854 g, m.p. 126-130° C., of ethylene 2-fluoro-2-phenyl-1,1-ethanedisulfonate (94-1).

To a solution of 3.5 g of ethylene methanedisulfonate in 60 mL of glyme and 0.9 g of NaH was added 3.4 g of 1-chloromethylnaphthalene followed by 2.6 g of NaI. The solution was stirred overnight and the glyme removed by the rotary evaporator at 20 mm pressure. The residue was taken up in an acid solution and CH$_2$Cl$_2$. The CH$_2$Cl$_2$ was rinsed with a NaHSO$_3$ solution, dried, concentrated, and cyclohexane was added to give 3.9 g (86%) of ethylene 2-naphthyl-1,1-ethanedisulfonate, m.p. 179-183° C. (94-2).

After the preparation of 94-4, the residue after the CH$_2$Cl$_2$ evaporation was taken up in NaHCO$_3$, filtered, and acidified to give ethylene (2-carboxy-benzoyl)-N-2-ethane-1,1-disulfonate, m.p. 111-120° C. (94-5).

To a solution of 1.4 g of ethylene methanedisulfonate in 50 mL of glyme with 0.2 g of NaH was added 1.1 g of 1,3-propanesulfonate. After 48 hrs., 50 mL of ether was added and 1.4 g (63%) of the sodium salt of butane-1-[hydroxyhydrogensulfate]-4,4-[ethylenedisulfonate] was recovered (94-9).

To a solution of ethylene 1-naphthylmethylmethanedisulfonate (94-2) in 50 mL of glyme and 0.6 g of NaH was added 1 g of acetyl chloride and the mixture was stirred overnight. The glyme was removed and the residue was taken up in CH$_2$Cl$_2$ and NaHCO$_3$ solution. From CH$_2$Cl$_2$ and cyclohexane there was obtained 1.65 g of crude product (82%), m.p. 128-162° C. Further crystallization gave 0.74 g, m.p. 158-174° C., of ethylene 2-naphthyl-1-acetyl-1,1-ethanedisulfonate (94-8).

The same procedure as for 94-2 was followed to give a 75% yield, m.p. 191-196° C. (95-2).

A solution of 0.9 g of ethylene methanedisulfonate in glyme with 0.13 g of NaH was filtered and 1.1 g of 9-bromofluorene was added. The reaction was very slow and was kept in a closed container for 21 days. Separation in CH$_2$Cl$_2$-cyclohexane gave 0.18 g of ethylene 9-fluorenylmethanedisulfonate, m.p. 118-124° C. (96-1).

A solution of 0.72 g of 95-2 and 0.14 g of NaH in 30 mL of glyme was stirred for 1 hr., then filtered and 0.41 g of ethylene sulfate was added. After 4 days the solvent was removed and the residue taken up in 5 mL of acetone, rinsed with acetone, and additional product obtained by concentration for a total of 0.9 g (84%) of the sodium salt of propane-1-[hydroxyhydrogensulfate]-3-(2-methylnaphthyl)-3,3-(ethylenedisulfonate) (96-14).

To a solution of 1.64 g of ethylene methanedisulfonate with 0.6 g of NaH in 50 mL of glyme was added 1.6 g of acetyl chloride. After 1 hr. of stirring the solution was filtered and the solvent removed. The residue was taken up in CH$_2$Cl$_2$ and H$_2$O. After the CH$_2$Cl$_2$ was separated and dried the addition of cyclohexane gave 1.06 g of a solid which was taken up in CH$_2$Cl$_2$ and treated with charcoal and cyclohexane to give 0.68 g of ethylene (2-methyl-2-acetyl)-ethylene-1,1-disulfonate, m.p. 143-152° C. (97-3).

To a solution of 1.4 g of ethylene methanedisulfonate in 50 mL of glyme and 0.45 g of NaH was added 1.5 g of monosolketalyl oxalyl chloride. After an hour a few drops of water in glyme was added and the solvent removed. The residue was taken up in 50 mL of CH$_2$Cl$_2$, to give 0.728 g of solid. Addition of cyclohexane to the CH$_2$Cl$_2$ gave an additional 0.816 g of the sodium salt of ethylene 2-hydroxy-2-solketalyl-ethylene-1,1-disulfonate (97-5).

To a solution of 0.78 g of 96-9 and 0.25 g of NaH in 50 mL of glyme was added 0.64 g of acetyl chloride. The mixture was stirred overnight, filtered, and the solvent removed to leave 0.75 g (58%) of crude product (97-7), ethylene acetyl-(3-methyl-1,4-naptho-2-quinolyl-1,1-ethanedisulfonate.

To a solution of 1.2 g of ethylene methanedisulfonate in 50 mL of glyme with 0.4 g of NaH was added, in large excess, 6.7 g of dichloromethyl methyl ether. The mixture was stirred for 2 days, filtered, and the solvent removed. The unreacted ester was removed by filtration from 5% NaHCO$_3$ and after removal of the water, the residue was taken up in acetone, the salts filtered, and the acetone evaporated to give 0.5 g of solid which, after drying, gave a m.p. of 142-146° C. (97-9), ethylene 2-methoxy-1,1-ethylenedisulfonate.

A solution of 96-9 was prepared as described except that only 0.04 g of NaI was used. The 96-9 was not isolated and 1.4 g of trifluoromethyl sulfonyl chloride was added. After stirring an hour the solution was filtered, the solvent removed, and the residue taken up in $CH_2Cl_2$, $H_2O$ washed, and the insoluble solid product filtered to give 0.95 g, m.p. 205-215 dec. (00-7), ethylene trifluorosulfonyl-(3-methyl-1,4-naphtho-2-quinolyl)-1,1-ethanedisulfonate.

The ester, 00-8, was prepared by the same method as 00-7, except that perfluorobutyryl chloride was used to give ethylene perfluorobutyril-(3-methyl-1,4-naphtho-2-quinoyl)-1,1-ethanedisulfonate (00-8). Using the same method with crotonoyl chloride gave 03-8.

To a solution of 2.02 g of ethylene methanedisulfonate and 1.5 g of 60% NaH was added 5.0 g of 2,3-dichloro-1,4-naphthoquinone. The solution was heated to 55-65° C. for 3 hrs, filtered, and the solvent removed. The residue was left open for 24 hrs while the excess NaH converted to $Na_2CO_3$. The residue was then triturated with 100 mL of cyclohexane. The washed residue was taken up in 100 mL of water and quickly filtered directly into a hydrochloric acid solution which was filtered and the dried solid, 2.35 g (56%) (03-1) of ethylene 3-chloro-1,4-naphtho-2-quinoylmethanedisulfonate, m.p. 198° C. dec., was obtained.

To a filtered solution of the 3-chloroquinonyl derivative, 0.78 g, in 50 mL of glyme with 0.3 g of NaH was added 0.3 g of crotonoyl chloride. The red solution was allowed to stand until the red color had changed to yellow, about 8 days. After solvent removal the residue was taken up in cyclohexane to give 0.886 g (96%) of ethylene crotonoyl-[3-chloro-1,4-naptho-2-quinolyl]-1,1-methanedisulfonate, m.p. 150-155° C. dec. (03-7).

To a solution of 0.98 g of the 3-chloroquinoyl derivative in 50 mL of glyme with 0.4 g of NaH was added 0.63 g of the oxalyl ester of solketal and the mixture was stirred for 5 days. After filtration and removal of the glyme, the residue was taken up in 25 mL of $CH_2Cl_2$. There was no insoluble solid; however, after removal of the $CH_2Cl_2$ and resolution in 15 mL of $CH_2Cl_2$ a sticky, insoluble gum was removed and the $CH_2Cl_2$ evaporated to leave 1.37 g (95%) of a waxy solid (05-5).

To a solution of 1.584 g of the ester 94-2 with 0.1 g of NaH in 25 mL of glyme was added 0.74 g (20% excess) of 2,2-dimethyl-1,3-dioxa-2-sila-4-thiacyclohexane-4,4-dioxide. After stirring overnight the solvent was removed and the residual solid suspended in 15 mL of ethanol, filtered, and rinsed to give 1.58 g (85%) of 94-7, m.p. partial at 175° C., resolidified and m.p. with dec. 220-225° C.

To a solution of 0.87 g of ethylenemethanedisulfonate with 0.13 g of NaH in 35 mL of glyme was added 0.98 g of the same silyl ester as in the previous preparation of 94-7. After two hours of stirring the solvent was removed and the residue triturated in 15 mL of EtOH to give 1.75 g (quantitative yield) of 94-6.

To a solution of 1.84 g of ethylene methanedisulfonate with 0.55 g of NaH in 60 mL of glyme was added 2.38 g of 1-naphthalenesulfonyl chloride. After an hour of stirring and the emission of a theoretical quantity of hydrogen the solution was decanted from a yellowish gum (0.73 g) and filtered through a pad of filteraid. The addition of 25 mL of ether produced more gum (0.574 g). A second addition of 40 mL of ether gave 1.686 g of solid. Further dilution with about 156 mL of ether gave a final 0.7 g of gum. The total quantity recovered was nearly theoretical in yield. The 1.686 g of solid was dissolved in water, and the solution was filtered through charcoal and evaporated to leave a dry residue of the sodium salt, 95-3.

To a solution of the ketone (95-6), 0.42 g in 40 mL of glyme with 0.05 g of NaH, was added 0.24 g of the silyl ester 2,2-dimethyl-1,3-dioxa-2-sila-4-thiacyclohexane-4,4-dioxide. The solution was stirred for two days, then filtered and the residue from evaporation of the filtrate was dissolved in 10 mL of $CH_2Cl_2$, filtered, and evaporated to give 0.289 g of 95-8.

To a solution of 0.86 g of ethylene methanedisulfonate with 0.1 g of NaH in 30 mL of glyme was added 0.45 g of

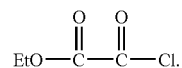

After stirring overnight and removal of the glyme, the residue was taken up in 5 mL of $CH_2Cl_2$ followed by the addition of 15 mL of cyclohexane to give 0.5015 g of 96-8, m.p. 128-160° C., dec. 165° C.

To a solution of 0.8 g of ethylene bromomethanedisulfonate (91-5) in 50 mL of glyme with 0.2 g of NaH was added followed by 0.6 g of the anhydride of 1,2-ethanedisulfonic acid. After 24 hrs, the solvent was removed and the residue taken up in 10 mL of acetone to give 0.5 g of water soluble 96-13.

To a solution of 0.8 g of ethylene methanedisulfonate in 60 mL of glyme with 0.4 g of NaH was added 0.8 g of α-chloro-α-hydroxy-o-toluenesulfonicacid-γ-sulfone. After 24 hrs, the solvent was removed and the residue taken up in 25 mL of $H_2O$, filtered, and rinsed with 10 mL of $H_2O$. To the filtrate was added 1.2 molar HCl dropwise and 0.4125 g of solid filtered. Trituration in 5 mL of $CH_2Cl_2$ gave 0.32 g of product (45% yield based on the fraction of ester recovered), m.p. 160-170° C. (96-16).

To a solution of 1.66 g of ethylene methanedisulfonate in 50 mL of glyme and 0.6 g of NaH was added 2 g of ethyl chloromethyl ether. The solution was stirred overnight, the solvent removed, and the residue taken up in 40 mL of $CH_2Cl_2$. This solution was washed with $H_2O$, and the $CH_2Cl_2$ was dried and removed to give 2.131 g of residue, m.p. 60-70° C., 81% yield. The product was further purified by crystallization from a 5% solution of cyclohexane and $CH_2Cl_2$ to give a product, m.p. 72-78° C. (97-2).

To a solution of 0.58 g of ethylene methanedisulfonate in 50 mL of glyme and 0.2 g of NaH was added 0.65 g of 8-quinolinesulfonyl chloride. After 3 hrs., the solution was filtered, and the solid was washed with $CH_2Cl_2$ and dried overnight to give 1.155 g of a mixture of NaCl, $Na_2CO_3$, and product. A sample was $H_2O$ soluble and the calculated yield, based on assumption of the NaCl and $Na_2CO_3$, was 0.848 g (71%) of 97-4.

To a solution of 0.386 g of 96-9 in 50 mL of glyme and 0.08 g of NaH was added 0.7 g of ethyl chloromethyl ether. After 24 hrs. the solution was filtered and the solvent removed from the filtrate. The residue was triturated with 10 mL of $CH_2Cl_2$, and the $CH_2Cl_2$ solution was washed with $H_2O$, dried, and concentrated to about 10 mL. The addition of 10 mL of cyclohexane gave 0.3 g of solid, m.p. 155-160° C. (27-6).

A solution of 1.35 g of 96-9 in 100 mL of glyme and 0.26 g of NaH was filtered after 1 hr., and to the filtrate was added 0.6 g of

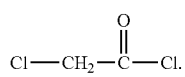

After an hour the solution was filtered through a pad of filteraid and the solvent removed to leave an oily residue. Trituration with 25 mL of cyclohexane gave 1.55 g (96%) of solid, m.p. 104-160° C. (03-3).

A solution of 0.845 g of 96-10 and 0.25 g of NaH in 50 mL of glyme was stirred until evolution of $H_2$ stopped, about 1 hr. The solution was filtered through a pad of filteraid and 0.3 g of crotonyl chloride was added. After stirring overnight, the NaCl was filtered, and the solvent was removed and the residue taken up in 100 mL of cyclohexane to give 0.769 g (78%) of 03-6.

To 1.01 g of ethylene methanedisulfonate in 50 mL of glyme with 0.6 g of NaH was added 2.8 g of solkalyloxalyl chloride. After stirring overnight the solution was filtered through a pad of filteraid and the residue after solvent removal was taken up in 25 mL of $CH_2Cl_2$, the solution filtered and washed with $CH_2Cl_2$ and the filtrate evaporated to give 2.55 g (90%) of waxy solid (05-2).

To a filteraid filtered solution of 1.3 g of 96-10 in 100 mL of glyme with 0.2 g of NaH was added 0.56 g of solkalyloxalyl chloride. After 24 hrs. reaction had not completed. After 5 days the solution was filtered to give 0.19 g of NaCl plus unreacted reagents. After removal of the solvent the residue slowly solidified to leave 1.16 g (76% yield) of 05-03.

To a solution of 0.97 g of 96-9 with 0.4 g of NaH in 50 mL of glyme was added 0.67 g of solkalyloxalyl chloride. After stirring overnight the solution was filtered through a pad of filteraid and removed. The residue was triturated with 15 mL of $CH_2Cl_2$, decanted, and rinsed with 5 mL of $CH_2Cl_2$. The $CH_2Cl_2$ was removed to leave 1.143 g of 05-04 (76% yield).

As described above, the derivatives of ethylene methanedisulfonate were found to be active as anticancer agents against one or more of the 65 or so cancers in initial screening. As such, and as described in the tables above, some of the derivatives were found to prevent growth of the cells to 30% or less at $10^{-4}$ molar concentrations, others shows similar anticancer activity at $10^{-5}$ molar or less and even others showed a lethal toxicity toward cancer cells at a level of 50% more at $10^4$ molar or less.

The compounds disclosed in this application includes various derivatives of ethylene methanedisulfonate with formula (I) or (II) as follows:

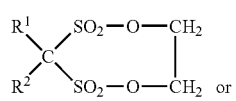 (I)

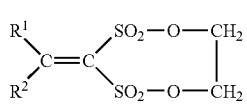 (II)

For example, a derivative of cyclic disulfonic ester compound as a cancer therapeutic agent comprise formula (I) wherein: $R^1$ is $H^-$, $CH_3CH_2$—O—$CH_2$—,

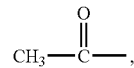

$CF_3SO_2^-$,

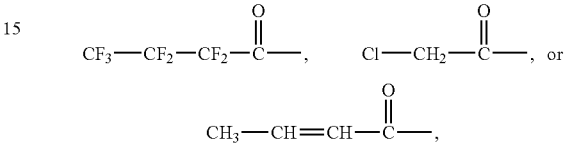

$R^2$ is a quinone moiety with a form of

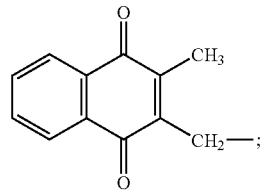

and the derivative with $R^1$=

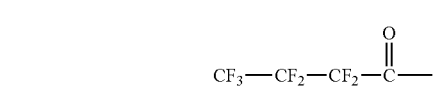

and $R^2$=

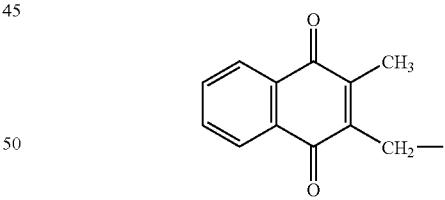

has increased lipophilicity compared to the cyclic disulfonic ester compound.

In another example, a derivative of cyclic disulfonic ester compound as a cancer therapeutic agent comprises formula (I) wherein $R^1$ is $H^-$, or

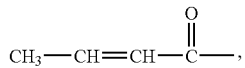

$R^2$ is a quinone moiety with a form of

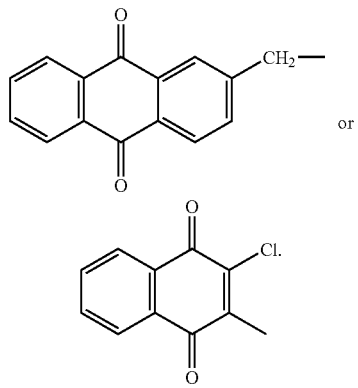 or

In another example, a derivative of cyclic disulfonic ester compound as a cancer therapeutic agent comprises formula (I) wherein $R^1$ and $R^2$ increase lipophilicity of the cyclic disulfonic ester compound where $R^1$ is a quinone moiety with a form of

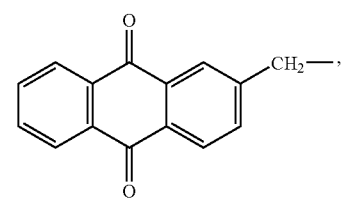

and $R^2$ is

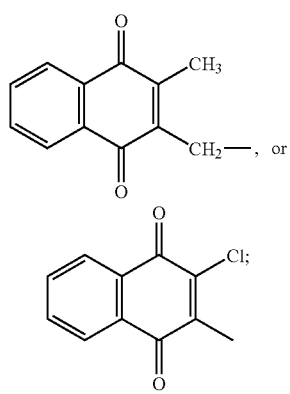

In another example, a derivative of cyclic disulfonic ester compound as a cancer therapeutic agent comprises formula (I) wherein $R^1$ and $R^2$ increase water solubility of the cyclic disulfonic ester compound where $R^1$ is H—; and $R^2$ is

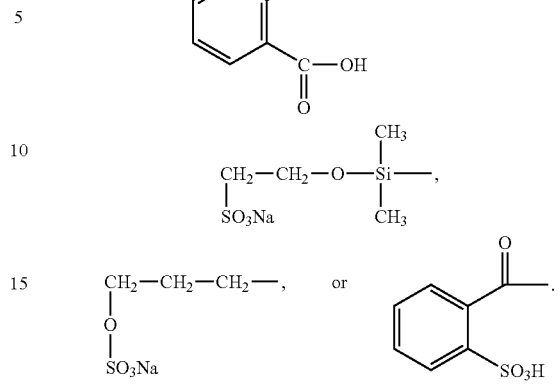

In another example, a derivative of cyclic disulfonic ester compound as a cancer therapeutic agent comprises formula (I) wherein $R^1$ and $R^2$ increase water solubility of the cyclic disulfonic ester compound where $R^1$ is

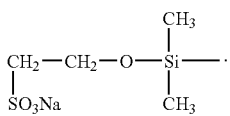

and $R^2$ is

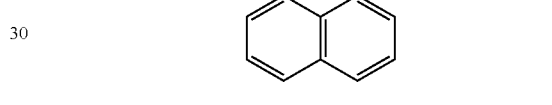

In another example, a derivative of cyclic disulfonic ester compound as a cancer therapeutic agent comprises formula (I) wherein $R^1$ and $R^2$ increase water solubility of the cyclic disulfonic ester compound where $R^1$ is Na$^+$; and $R^2$ is

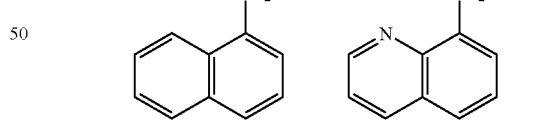

In another example, a derivative of cyclic disulfonic ester compound as a cancer therapeutic agent comprises formula (I) wherein $R^1$ and $R^2$ increase water solubility of the cyclic disulfonic ester compound where $R^1$ is

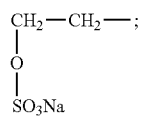

and $R^2$ is

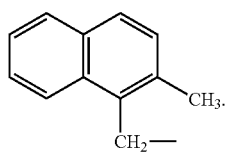

In another example, a derivative of cyclic disulfonic ester compound as a cancer therapeutic agent comprises formula (II) wherein $R^1$ and $R^2$ increase water solubility of the cyclic disulfonic ester compound where $R^1$ is

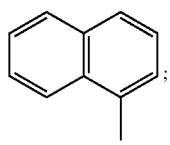

and $R^2$ is

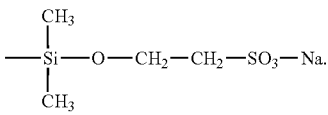

In another example, a derivative of cyclic disulfonic ester compound as a cancer therapeutic agent comprises formula (III)

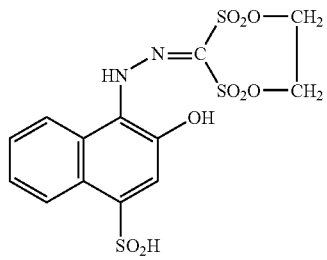

wherein the derivative has increased water solubility compared to the cyclic disulfonic ester compound.

In another example, a derivative of cyclic disulfonic ester compound as a cancer therapeutic agent comprises formula (II) wherein $R^1$ and $R^2$ increase water solubility and lipophilicity of the cyclic disulfonic ester compound where $R^1$ is

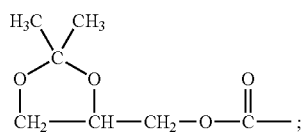

and $R^2$ is —ONa, or

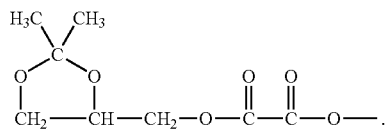

In another example, a derivative of cyclic disulfonic ester compound as a cancer therapeutic agent comprises formula (II) wherein $R^1$ and $R^2$ increase water solubility of the cyclic disulfonic ester compound where $R^1$ is H—; and $R^2$ is —OCH3.

In another example, a derivative of cyclic disulfonic ester compound as a cancer therapeutic agent comprises formula (I) wherein $R^1$ and $R^2$ increase water solubility of the cyclic disulfonic ester compound, where $R^1$ is bromine; and $R^2$ is

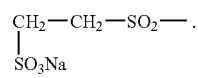

In another example, a derivative of cyclic disulfonic ester compound as a cancer therapeutic agent comprises formula (I) wherein $R^1$ and $R^2$ increase lipophilicity of the cyclic disulfonic ester compound, where $R^1$ is

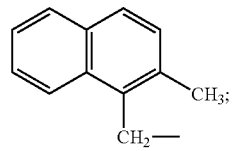

and $R^2$ is

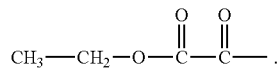

In another example, a derivative of cyclic disulfonic ester compound as a cancer therapeutic agent comprises formula (I) wherein $R^1$ and $R^2$ increase the potential for halogenation of the cyclic disulfonic ester compound, where $R^1$ is H—; and $R^2$ is a halogen selected from the group consisting of florine, bromine, and iodine.

In another example, a derivative of cyclic disulfonic ester compound as a cancer therapeutic agent comprises formula (I) wherein $R^1$ and $R^2$ increase the potential for halogenation of the cyclic disulfonic ester, where compound $R^1$ is the same as $R^2$, and $R^1$ and $R^2$ is a halogen selected from the group consisting of chlorine, bromine, and iodine.

In another example, a derivative of cyclic disulfonic ester compound as a cancer therapeutic agent comprises formula (I) wherein $R^1$ and $R^2$ increase the potential for halogenation of the cyclic disulfonic ester, where $R^1$ is fluorine; and $R^2$ is bromine or

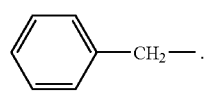

In another example, a derivative of cyclic disulfonic ester compound as a cancer therapeutic agent comprises formula (I) wherein $R^1$ and $R^2$ increase the potential for halogenation of the cyclic disulfonic ester, where $R^1$ is iodine; and $R^2$ is

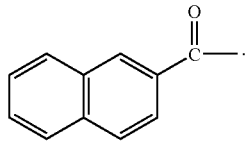

In another example, a derivative of cyclic disulfonic ester compound as a cancer therapeutic agent comprises formula (I) wherein $R^1$ and $R^2$ increase the potential for halogenation of the cyclic disulfonic ester, where $R^1$ is bromine; and $R^2$ is

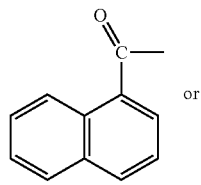 or

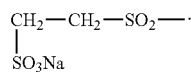

In another example, a derivative of cyclic disulfonic ester compound as a cancer therapeutic agent comprises formula (I) wherein the derivative is a cancer cell stimulator and cancer cell inhibitor, where $R^1$ is H—; and $R^2$ is

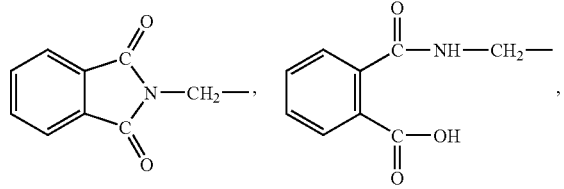

$CH_3$—, F—, $CH_3(CH_2)_6CH_2$—O—$CH_2$—, or

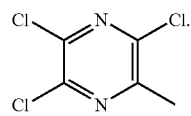

In another example, a derivative of cyclic disulfonic ester compound as a cancer therapeutic agent comprises formula (I) wherein $R^1$ is hydrogen; and $R^2$ is

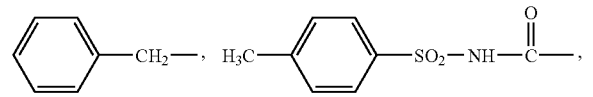

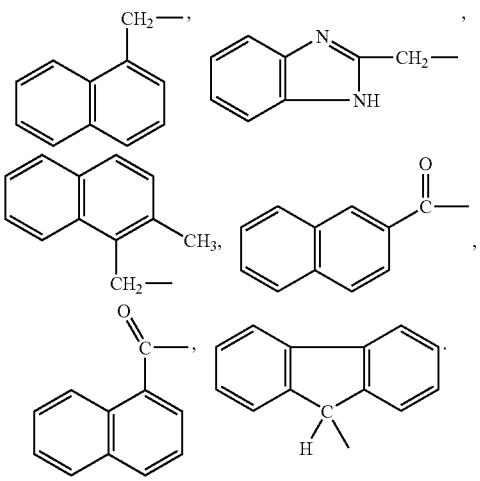

In another example, a derivative of cyclic disulfonic ester compound as a cancer therapeutic agent comprises formula (I) wherein $R^1$ is —$CH_2CH_2CN$; and $R^2$ is —$CH_2CH_2CN$.

In another example, a derivative of cyclic disulfonic ester compound as a cancer therapeutic agent comprises formula (I) wherein $R^1$ is

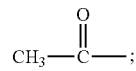

and $R^2$ is

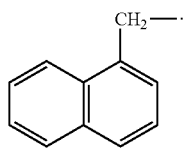

In another example, a derivative of cyclic disulfonic ester compound as a cancer therapeutic agent comprises formula (I) wherein $R^1$ is $CH_3CH_2$—O—$CH_2$—; and $R^2$ is $CH_3CH_2$—O—$CH_2$—.

In another example, a derivative of cyclic disulfonic ester compound as a cancer therapeutic agent comprises formula (II) wherein $R^1$ is $CH_3$—; and $R^2$ is

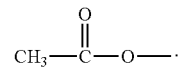

A method is also provided for synthesis of a derivative of ethylene methanedisulfonate of formula (I)

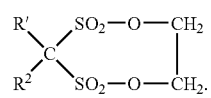

The method comprises a step of removing an active hydrogen of ethylene methanedisulfonate with NaH to replace the active hydrogen with Na in an reaction. In one embodiment, excess amount of NaH may be used in the reaction.

In another example, a method is provided for synthesis of a derivative of ethylene methanedisulfonate of formula (I)

$$\begin{array}{c} R' \\ \diagdown \\ C \\ \diagup \\ R^2 \end{array} \begin{array}{c} SO_2-O-CH_2 \\ | \\ SO_2-O-CH_2 \end{array}$$

The method comprises a step of reacting one or more electrophilic reagents with alkali salts of ethylene methanedisulfonate wherein electrophilic reagents comprises aliphatic carboxylic acid halides, aromatic carboxylic acid halides, sulfonyl halides, imidohalides, or activated halides.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring, nor excluding, two or more such elements.

Inventions embodied in various combinations and subcombinations of features, functions, elements, and/or properties may be claimed in a related application. Such claims, whether they are directed to a different invention or directed to the same invention, whether different, broader, narrower or equal in scope to any original claims, are also regarded as included within the subject matter of the inventions of the present disclosure.

We claim:

1. A compound comprising formula:

$$\begin{array}{c} R' \\ \diagdown \\ C \\ \diagup \\ R^2 \end{array} \begin{array}{c} SO_2-O-CH_2 \\ | \\ SO_2-O-CH_2 \end{array} \quad (I)$$

wherein:
$R^1$ is H−, $CH_3CH_2-O-CH_2-$, $$CH_3-\overset{O}{\underset{\|}{C}}-,$$

$CF_3SO_2^-$, $$CF_3-CF_2-CF_2-\overset{O}{\underset{\|}{C}}-, \quad Cl-CH_2-\overset{O}{\underset{\|}{C}}-,$$

or $$CH_3-CH=CH-\overset{O}{\underset{\|}{C}}-; \quad \text{and}$$

$R^2$ is

[naphthoquinone with CH$_3$ and CH$_2$— substituents].

2. A compound comprising formula (I):

$$\begin{array}{c} R' \\ \diagdown \\ C \\ \diagup \\ R^2 \end{array} \begin{array}{c} SO_2-O-CH_2 \\ | \\ SO_2-O-CH_2 \end{array} \quad (I)$$

wherein:
$R^1$ is H−, or $$CH_3-CH=CH-\overset{O}{\underset{\|}{C}}-; \quad \text{and}$$

$R^2$ is

[anthraquinone-CH$_2$—] or [naphthoquinone with Cl and CH$_3$ substituents].

3. A compound with formula (I):

$$\begin{array}{c} R^1 \\ \diagdown \\ C \\ \diagup \\ R^2 \end{array} \begin{array}{c} SO_2-O-CH_2 \\ | \\ SO_2-O-CH_2 \end{array} \quad (I)$$

where
$R^1$ is

[anthraquinone-CH$_2$—],

[naphthoquinone with CH$_3$ and CH$_2$— substituents], or [naphthoquinone with Cl and CH$_3$ substituents], and
R² is

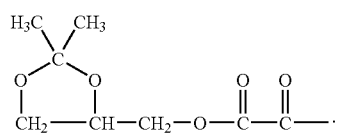

4. A compound with formula (II):

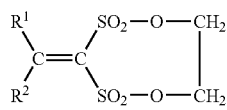

where
R¹ is

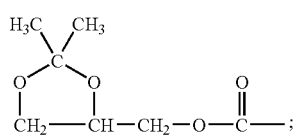

and R² is —ONa, or

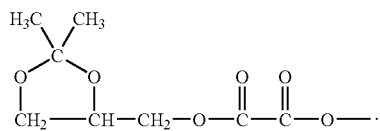

5. A compound with formula (I):

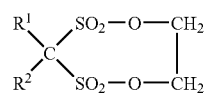

where
R¹ is

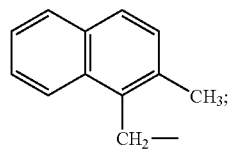

and R² is $$CH_3-CH_2-O-\overset{O}{\underset{\|}{C}}-\overset{O}{\underset{\|}{C}}-.$$

6. A method for synthesis of a derivative of ethylene methanedisulfonate of formula (I):

 (I)

comprising a step of removing an active hydrogen of ethylene methanedisulfonate with NaH to replace the active hydrogen with Na or other radicals in a reaction, where R² is

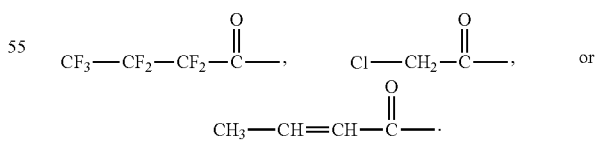

and where R¹ is $CH_3CH_2-O-CH_2-$, $$CH_3-\overset{O}{\underset{\|}{C}}-,$$

$CF_3SO_2^-$, $$CF_3-CF_2-CF_2-\overset{O}{\underset{\|}{C}}-, \quad Cl-CH_2-\overset{O}{\underset{\|}{C}}-, \quad \text{or}$$

$$CH_3-CH=CH-\overset{O}{\underset{\|}{C}}-.$$

7. The method of claim 6, wherein excess amount of NaH is used in the reaction.

* * * * *